United States Patent [19]

Thomas et al.

[11] Patent Number: 5,789,220
[45] Date of Patent: Aug. 4, 1998

[54] PRODUCTION OF γ-LINOLENIC ACID BY A Δ6-DESATURASE

[75] Inventors: Terry L. Thomas, College Station; Avutu S. Reddy, Bryan; Michael Nuccio, College Station; Andrew N. Nunberg, Bryan, all of Tex.; Georges L. Freyssinet, Saint Cyr au mont d'or, France

[73] Assignee: Rhone-Poulenc Agrochimie, Lyon, France

[21] Appl. No.: 789,936

[22] Filed: Jan. 28, 1997

Related U.S. Application Data

[63] Continuation of Ser. No. 366,779, Dec. 30, 1994, Pat. No. 5,614,393, which is a continuation-in-part of Ser. No. 307,382, Sep. 14, 1994, Pat. No. 5,552,306, which is a continuation of Ser. No. 959,952, Oct. 13, 1992, abandoned, which is a continuation-in-part of Ser. No. 817,919, Jan. 8, 1992, abandoned, which is a continuation-in-part of Ser. No. 774,475, Oct. 10, 1991, abandoned.

[51] Int. Cl.$^6$ ..................................... C12N 9/50
[52] U.S. Cl. .................. 435/189; 536/23.2; 435/219; 435/69.1; 435/183; 530/350
[58] Field of Search ..................... 536/23.2, 23.6; 435/134, 189, 69.1, 91.1, 172.1, 172.3, 320.1, 375, 183

[56] References Cited

U.S. PATENT DOCUMENTS 5,614,393  3/1997  Thomas et al. ..................... 435/134

OTHER PUBLICATIONS

Griffiths et al. Delta-6 and Delta-12 Desaturase Activities and Phosphatidic Acid Formation in Microsomal Preparations from the Developing Cotyledons of Common Borage (Borago Officinalis). Biochemical Journal, vol. 252, pp. 641–647, 1988.

Stymne et al. Biosynthesis of Gamma-Linolenic Acid in Cotyledons and Microsomal Preparations of the Developing Seeds of Common Borage (Borago Officinalis). Biochemical Journal, vol. 240, pp. 385–393, 1986.

O. Sayonova et al. PNAS 94: 4211–6, Apr. 1997.

*Primary Examiner*—Jasemine C. Chambers
*Assistant Examiner*—Deborah J. R. Clark
*Attorney, Agent, or Firm*—Scully, Scott, Murphy & Presser

[57] ABSTRACT

Linoleic acid is converted into γ-linolenic acid by the enzyme Δ6-desaturase. The present invention is directed to isolated nucleic acids comprising the Δ6-desaturase gene. More particularly, the isolated nucleic acid comprises the promoter, coding region and termination regions of the Δ6-desaturase gene. The present invention provides recombinant constructions comprising the Δ6-desaturase coding region in functional combination with heterologous regulatory sequences. The nucleic acids and recombinant constructions of the instant invention are useful in the production of GLA in transgenic organisms.

1 Claim, 8 Drawing Sheets

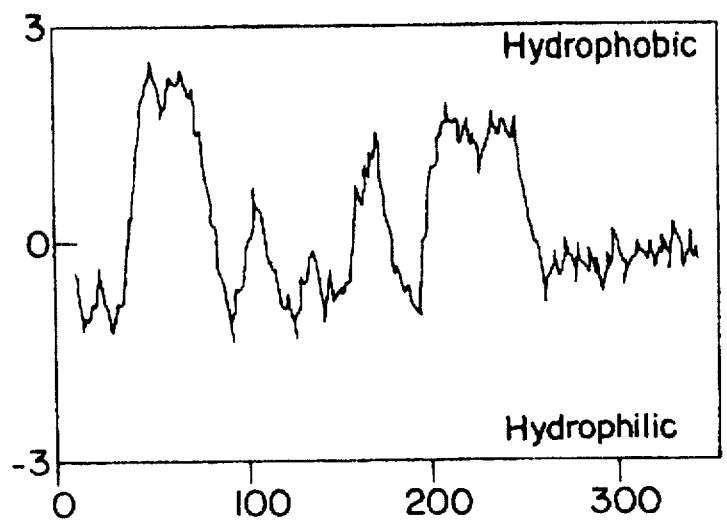
FIG. IA
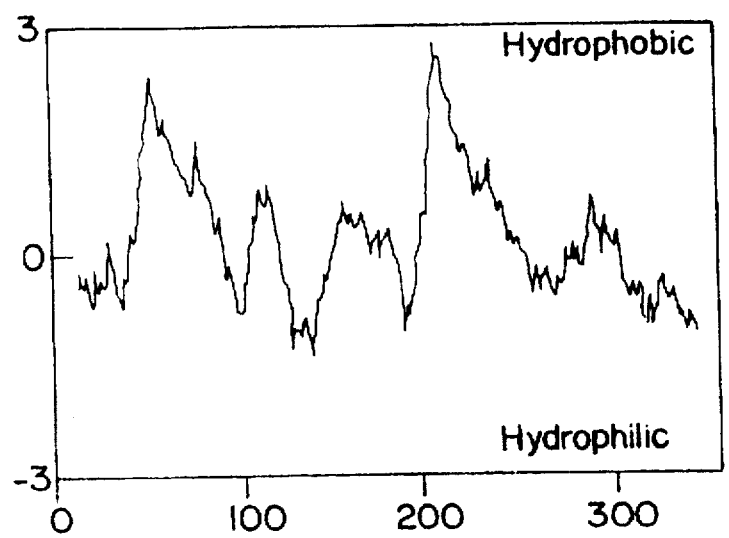
FIG. IB

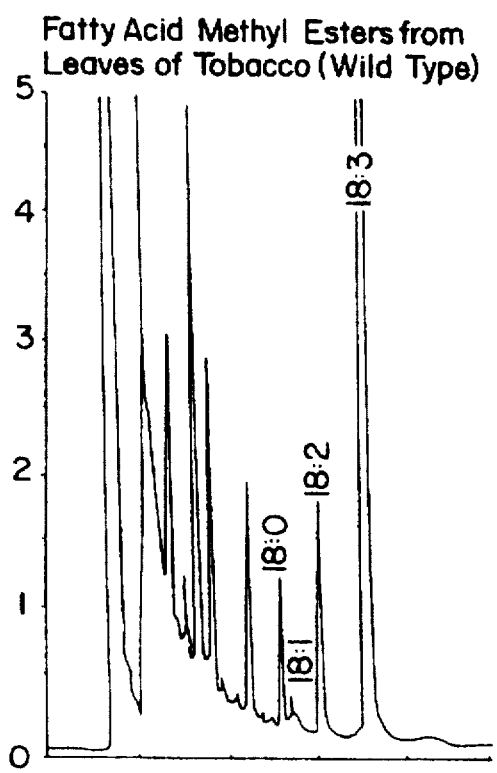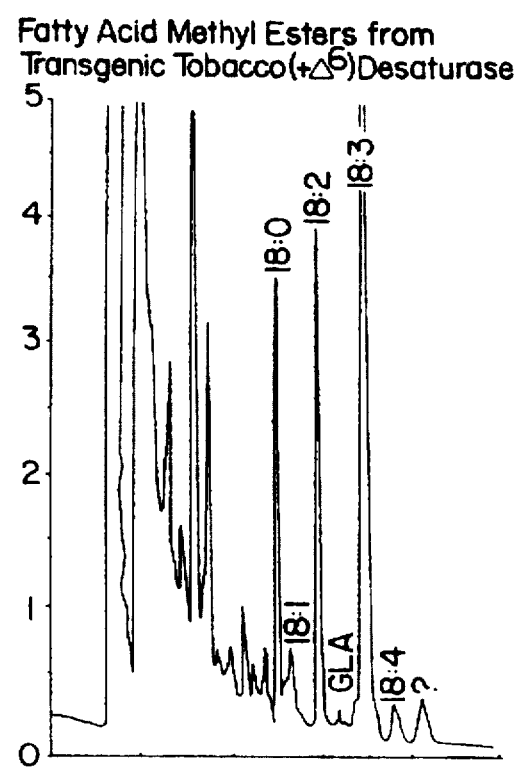
FIG. 4A
FIG. 4B

FIG.5A

```
   1 aatatctgcc taccctccca aagagagtag tcattttca tcaatgctg ctcaaatcaa gaaatacatt acctcagatg   80
  81 aactcaagaa ccacgataaa cccggagatc tatggatctc gattcaaggg aaagcctatg tttgttcgga tggtgaaa  160
 161 gaccatccag gtggcagctt tcccttgaag agtcttgctg gtcaagaggt aactgatgca tttgttgcat tccatcctgc  240
 241 ctctacatgg aagaatcttg atatgttttt cactgggtat tatcttaaag attactctgt ttctgaggtt tctaaagatt  320
 321 ataggaagct tgtgtttgag tgtgttgta tggtttttgt tgacaaaaaa ggtcatatta tgtttgcaac tttgtgcttt  400
 401 atagcaatgc tgtttgctat gagtgttggg gattgacat tttgtgaggg tgtttggta cattgtttt ctgggtgttt  480
 481 gatgggtttt ctttgattc agagtgttgt gctgcaaatt gtctttcagg gatgctggc attatatggt agtgtctgat  560
 561 ataagtttat gggtatttt tgaatatgac cctgattac aataagtatt ggttggtgga aatgaaacca taatgcacat  640
 641 cacattgcct gtaatagcct tctcattct atgagaaaag gttgactttt caagatcttt gtgtcttcca agttttttgg  720
 721 ttcactcacc tctcattatt gctgctaggc tcaatatgta tgtacaatct ccgttgactt gttgaccaa gagaaatgtg  800
 801 catttaccc tattatgtgt cttgggatgc cttggaaagc tttatcagtg cagttcagtt ccgttgcttt gttccttgtt  880
 881 tcctatcgag ctcaggaact tttatcagtg tttatcagtg tttatcagtg actgaatgc gtcctcctg aaccactct   960
 961 gggtgaaaga attatgtttg ttattgaag aagcctaaag gttgagaaa caaacgatg ggacacttga cattcctgt  1040
1041 cttcaagtgt ctggattgtt tcatggttga ttgcaattcc aaattgagca tcatttgttt cccaagatgc ctagatgcaa  1120
1121 cctcctagga atctcgccct acgtgatcga gttatgcaag aaacataatt tgcctacca gatataacca agccgctccc  1200
1201 ccaatgaaat gacactccga acactgagga acaccagcat gcaggctagg gatataattt agttcatgta attatgtatc  1280
1281 gtatgggaag ctcttcacac aattaccctt agtteetttat ggtttattag atgttttta atatatttta  1360
1361 gtgtcttgtc ttggttctac ttgttggagt cattgtgaaa caattgtgt gctcaaatatc tgatatttg  1440
1441 gagtttttgc tttcatctcc attattgatg aataaggagt tttaaatgga tttaaaatgt gctacttct  1520
1521 gaatgtactt tgtaccactg tgttttcagt tgaagctcat atagactttg atagactttg tttaaatggt tatgtcatgt  1680
1681 tattt                                                                                  1685
```

FIG.5B

```
  1 MAAQIKKYIT SDELKNHDKP GDLWISIQGK AYDVSDWVKD HPGGSFPLKS LAGQEVTDAF VAFHPASTWK NLDKFFTGYY   80
 81 LKDYSVSEVS KDYRKLVFEF SKMGLYDKKG HIMFATLCFI AMLFAMSVYG VLFCEGVLVH LFSGCLMGFL WIQSGWIGHD  160
161 IACNSLEYDP DLQYIPFLVV SSKFFGSLTS HFYEKRLTFD  240
161 AGHYMVVSDS RLNKFMGIFA ANCLSGISIG WWKWNHNAHH
241 SLSRFFVSYQ HWTFYPIMCA ARLNMYVQSL IMLLTKRNVS YRAQELLGCL VFSIWYPLLV SCLPNWGERI MFVIASLSVT  320
321 GMQQVQFSLN HFSSSVYVGK PKGNNWFEKQ TDGTLDISCP PWMDWFHGGL QFQIEHHLFP KMPRCNLRKI SPYVIELCKK  400
401 HNLPYNYASF SKANEMTLRT LRNTALQARD ITKPLPKNLV WEALHTHG                                    448
```

FIG. 8A
FIG. 8B
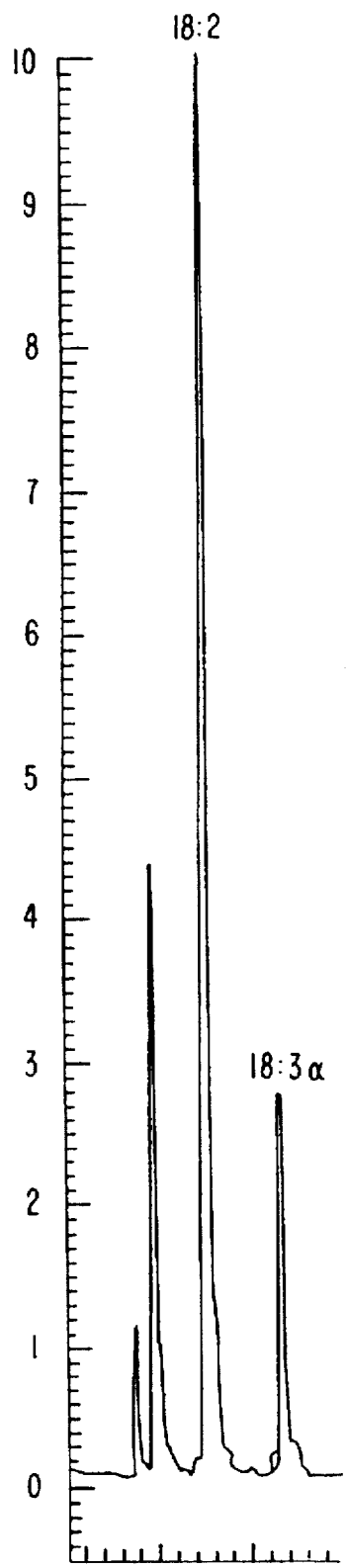
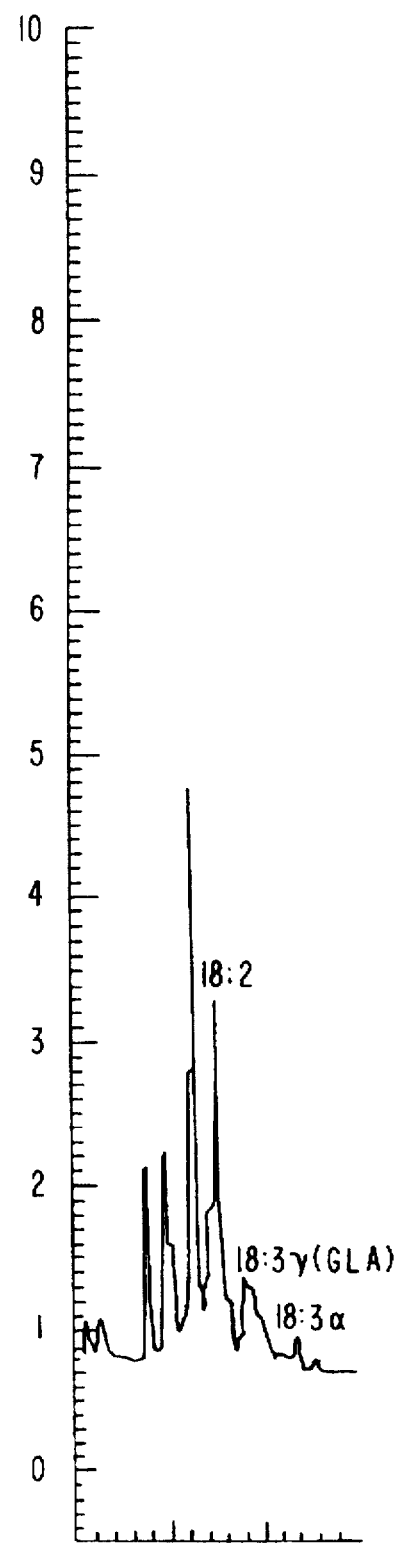

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 3588 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 2002..3081

( x i ) SEQUENCE DESCRIPTION: SEQ ID NO:1:

```
GCTAGCCACC  AGTGACGATG  CCTTGAATTT  GGCCATTCTG  ACCCAGGCCC  GTATTCTGAA      60
TCCCCGCATT  CGCATTGTTA  ATCGTTTGTT  CAACCATGCC  CTGGGTAAAC  GTTAGACAC      120
CACCTTGCCA  GACCACGTTA  GTTGAGTGT   TTCCGCCCTG  GCGGCCCCGA  TTTTTTCCTT     180
TGCGGCTTTG  GGCAATCAGG  CGATCGGGCA  ATTGCGTTTG  TTTGACCAGA  CTTGGCCCAT     240
TCAGGAAATT  GTCATTCACC  AAGACCATCC  CTGGCTCAAT  TTACCCCTGG  CGGATTTATG     300
GGATGATCCG  AGCCGAATGT  TGATCTATTA  CCTACCGGCC  CACAGTGAAA  CGGATTTAGT     360
AGGCGCAGTG  GTGAATAATT  TAACGTTGCA  ATCTGGGGAC  CATTTAATAG  TGGGACAAAA     420
ACCCCAACCC  AAGACCAAAC  GGCGATCGCC  TTGGCGCAAA  TTTTCCAAAC  TGATTACCAA     480
CCTGCGGGAG  TATCAGCGGT  ATGTCCAACA  GGTGATATGG  GTGGTGTTGT  TTTTATTGTT     540
GATGATTTTT  CTGGCCACCT  TCATCTACGT  TTCCATTGAT  CAACATATTG  CCCCAGTGGA     600
CGCGTTGTAT  TTTTCCGTGG  GCATGATTAC  CGGGGCCGGT  GGCAAGGAAG  AGGTGGCCGA     660
AAAGTCCCCC  GATATCATCA  AAGTATTCAC  AGTGGTGATG  ATGATCGCCG  GGGCGGGGGT     720
GATTGGTATT  TGTTATGCCC  TACTGAATGA  TTTCATCCTT  GGCAGTCGCT  TTAGTCAGTT     780
TTTGGATGCG  GCCAAGTTAC  CCGATCGCCA  TCACATCATC  ATTTGTGGGC  TGGGGGGAGT     840
GAGCATGGCC  ATTATTGAAG  AGTTAATTCA  CCAGGGCCAT  GAAATTGTGG  TAATCGAAAA     900
GGATACAGAT  AATCGTTTCT  TGCATACGGC  CCGCTCCCTG  GGGGTGCCCG  TAATTGTGGA     960
GGATGCCCGC  CTAGAAAGAA  CGTTGGCCTG  CGCCAATATC  AACCGAGCCG  AAGCCATTGT    1020
GGTGGCCACC  AGCGACGACA  CCGTTAACTT  GGAAATTGGC  CTAACTGCCA  AGGCGATCGC    1080
CCCTAGCCTG  CCAGTGGTGT  TGCGTTGCCA  GGATGCCCAG  TTTAGCCTGT  CCCTGCAGGA    1140
AGTATTTGAA  TTTGAAACGG  TGCTTTGTCC  GGCGGAATTG  GCCACCTATT  CCTTTGCGGC    1200
GGCGGCCCTG  GGGGGCAAAA  TTTTGGGCAA  CGGCATGACC  GATGATTTGC  TGTGGGTAGC    1260
CCTAGCCACC  TTAATCACTC  CTAACCATCC  CTTTGCCGAC  CAATTGGTTA  AAATTGCAGC    1320
CCAAAAGTCT  GATTTCGTTC  CCCTCTATCT  AGAACGGGGT  GGCAAAACCA  TCCATAGCTG    1380
GGAATTATTG  GGTACCCATC  TCGACTCTGG  AGACGTGTTG  TATTTAACCA  TGCCCGCCAC    1440
TGCCCTAGAG  CAACTTTGGC  GATCGCCCCG  TGCCACTGCT  GATCCTCTGG  ACTCTTTTTT    1500
```

```
GGTTTAGCAT GGGGGGATGG AACTCTTGAC TCGGCCCAAT GGTGATCAAG AAAGAACGCT        1560

TTGTCTATGT TTAGTATTTT TAAGTTAACC AACAGCAGAG GATAACTTCC AAAAGAAATT        1620

AAGCTCAAAA AGTAGCAAAA TAAGTTTAAT TCATAACTGA GTTTACTGC TAAACAGCGG         1680

TGCAAAAAAG TCAGATAAAA TAAAAGCTTC ACTTCGGTTT TATATTGTGA CCATGGTTCC       1740

CAGGCATCTG CTCTAGGGAG TTTTTCCGCT GCCTTTAGAG AGTATTTCT CCAAGTCGGC        1800

TAACTCCCCC ATTTTTAGGC AAAATCATAT ACAGACTATC CCAATATTGC CAGAGCTTTG      1860

ATGACTCACT GTAGAAGGCA GACTAAAATT CTAGCAATGG ACTCCCAGTT GGAATAAATT      1920

TTTAGTCTCC CCCGGCGCTG GAGTTTTTTT GTAGTTAATG GCGGTATAAT GTGAAAGTTT      1980

TTTATCTATT TAAATTTATA A ATG CTA ACA GCG GAA AGA ATT AAA TTT ACC        2031
             Met Leu Thr Ala Glu Arg Ile Lys Phe Thr
               1               5                   10

CAG AAA CGG GGG TTT CGT CGG GTA CTA AAC CAA CGG GTG GAT GCC TAC        2079
Gln Lys Arg Gly Phe Arg Arg Val Leu Asn Gln Arg Val Asp Ala Tyr
            15              20                  25

TTT GCC GAG CAT GGC CTG ACC CAA AGG GAT AAT CCC TCC ATG TAT CTG        2127
Phe Ala Glu His Gly Leu Thr Gln Arg Asp Asn Pro Ser Met Tyr Leu
        30              35                  40

AAA ACC CTG ATT ATT GTG CTC TGG TTG TTT TCC GCT TGG GCC TTT GTG        2175
Lys Thr Leu Ile Ile Val Leu Trp Leu Phe Ser Ala Trp Ala Phe Val
    45              50                  55

CTT TTT GCT CCA GTT ATT TTT CCG GTG CGC CTA CTG GGT TGT ATG GTT        2223
Leu Phe Ala Pro Val Ile Phe Pro Val Arg Leu Leu Gly Cys Met Val
60              65                  70

TTG GCG ATC GCC TTG GCG GCC TTT TCC TTC AAT GTC GGC CAC GAT GCC        2271
Leu Ala Ile Ala Leu Ala Ala Phe Ser Phe Asn Val Gly His Asp Ala
75              80                  85                  90

AAC CAC AAT GCC TAT TCC TCC AAT CCC CAC ATC AAC CGG GTT CTG GGC        2319
Asn His Asn Ala Tyr Ser Ser Asn Pro His Ile Asn Arg Val Leu Gly
            95              100                 105

ATG ACC TAC GAT TTT GTC GGG TTA TCT AGT TTT CTT TGG CGC TAT CGC        2367
Met Thr Tyr Asp Phe Val Gly Leu Ser Ser Phe Leu Trp Arg Tyr Arg
        110             115                 120

CAC AAC TAT TTG CAC CAC ACC TAC ACC AAT ATT CTT GGC CAT GAC GTG        2415
His Asn Tyr Leu His His Thr Tyr Thr Asn Ile Leu Gly His Asp Val
        125             130                 135

GAA ATC CAT GGA GAT GGC GCA GTA CGT ATG AGT CCT GAA CAA GAA CAT        2463
Glu Ile His Gly Asp Gly Ala Val Arg Met Ser Pro Glu Gln Glu His
140             145                 150

GTT GGT ATT TAT CGT TTC CAG CAA TTT TAT ATT TGG GGT TTA TAT CTT        2511
Val Gly Ile Tyr Arg Phe Gln Gln Phe Tyr Ile Trp Gly Leu Tyr Leu
155             160                 165                 170

TTC ATT CCC TTT TAT TGG TTT CTC TAC GAT GTC TAC CTA GTG CTT AAT        2559
Phe Ile Pro Phe Tyr Trp Phe Leu Tyr Asp Val Tyr Leu Val Leu Asn
        175             180                 185

AAA GGC AAA TAT CAC GAC CAT AAA ATT CCT CCT TTC CAG CCC CTA GAA        2607
Lys Gly Lys Tyr His Asp His Lys Ile Pro Pro Phe Gln Pro Leu Glu
        190             195                 200

TTA GCT AGT TTG CTA GGG ATT AAG CTA TTA TGG CTC GGC TAC GTT TTC        2655
Leu Ala Ser Leu Leu Gly Ile Lys Leu Leu Trp Leu Gly Tyr Val Phe
        205             210                 215

GGC TTA CCT CTG GCT CTG GGC TTT TCC ATT CCT GAA GTA TTA ATT GGT        2703
Gly Leu Pro Leu Ala Leu Gly Phe Ser Ile Pro Glu Val Leu Ile Gly
220             225                 230

GCT TCG GTA ACC TAT ATG ACC TAT GGC ATC GTG GTT TGC ACC ATC TTT        2751
Ala Ser Val Thr Tyr Met Thr Tyr Gly Ile Val Val Cys Thr Ile Phe
235             240                 245                 250
```

```
ATG CTG GCC CAT GTG TTG GAA TCA ACT GAA TTT CTC ACC CCC GAT GGT                    2799
Met Leu Ala His Val Leu Glu Ser Thr Glu Phe Leu Thr Pro Asp Gly
            255             260             265

GAA TCC GGT GCC ATT GAT GAC GAG TGG GCT ATT TGC CAA ATT CGT ACC                    2847
Glu Ser Gly Ala Ile Asp Asp Glu Trp Ala Ile Cys Gln Ile Arg Thr
        270             275             280

ACG GCC AAT TTT GCC ACC AAT AAT CCC TTT TGG AAC TGG TTT TGT GGC                    2895
Thr Ala Asn Phe Ala Thr Asn Asn Pro Phe Trp Asn Trp Phe Cys Gly
        285             290             295

GGT TTA AAT CAC CAA GTT ACC CAC CAT CTT TTC CCC AAT ATT TGT CAT                    2943
Gly Leu Asn His Gln Val Thr His His Leu Phe Pro Asn Ile Cys His
        300             305             310

ATT CAC TAT CCC CAA TTG GAA AAT ATT ATT AAG GAT GTT TGC CAA GAG                    2991
Ile His Tyr Pro Gln Leu Glu Asn Ile Ile Lys Asp Val Cys Gln Glu
315             320             325             330

TTT GGT GTG GAA TAT AAA GTT TAT CCC ACC TTC AAA GCG GCG ATC GCC                    3039
Phe Gly Val Glu Tyr Lys Val Tyr Pro Thr Phe Lys Ala Ala Ile Ala
            335             340             345

TCT AAC TAT CGC TGG CTA GAG GCC ATG GGC AAA GCA TCG TGACATTGCC                     3088
Ser Asn Tyr Arg Trp Leu Glu Ala Met Gly Lys Ala Ser
        350             355             360

TTGGGATTGA AGCAAAATGG CAAAATCCCT CGTAAATCTA TGATCGAAGC CTTTCTGTTG                  3148

CCCGCCGACC AAATCCCCGA TGCTGACCAA AGGTTGATGT GGCATTGCT  CCAAACCCAC                  3208

TTTGAGGGGG TTCATTGGCC GCAGTTTCAA GCTGACCTAG GAGGCAAAGA TTGGGTGATT                  3268

TTGCTCAAAT CCGCTGGGAT ATTGAAAGGC TTCACCACCT TTGGTTTCTA CCCTGCTCAA                  3328

TGGGAAGGAC AAACCGTCAG AATTGTTTAT TCTGGTGACA CCATCACCGA CCCATCCATG                  3388

TGGTCTAACC CAGCCCTGGC CAAGGCTTGG ACCAAGGCCA TGCAAATTCT CCACGAGGCT                  3448

AGGCCAGAAA AATTATATTG GCTCCTGATT TCTTCCGGCT ATCGCACCTA CCGATTTTTG                  3508

AGCATTTTTG CCAAGGAATT CTATCCCCAC TATCTCCATC CCACTCCCCC GCCTGTACAA                  3568

AATTTTATCC ATCAGCTAGC                                                              3588
```

( 2 ) INFORMATION FOR SEQ ID NO:2:

( i ) SEQUENCE CHARACTERISTICS:
        ( A ) LENGTH: 359 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Thr Ala Glu Arg Ile Lys Phe Thr Gln Lys Arg Gly Phe Arg
 1              5              10              15

Arg Val Leu Asn Gln Arg Val Asp Ala Tyr Phe Ala Glu His Gly Leu
            20             25             30

Thr Gln Arg Asp Asn Pro Ser Met Tyr Leu Lys Thr Leu Ile Ile Val
        35             40             45

Leu Trp Leu Phe Ser Ala Trp Ala Phe Val Leu Phe Ala Pro Val Ile
    50             55             60

Phe Pro Val Arg Leu Leu Gly Cys Met Val Leu Ala Ile Ala Leu Ala
65             70             75             80

Ala Phe Ser Phe Asn Val Gly His Asp Ala Asn His Asn Ala Tyr Ser
            85             90             95

Ser Asn Pro His Ile Asn Arg Val Leu Gly Met Thr Tyr Asp Phe Val
           100            105            110

Gly Leu Ser Ser Phe Leu Trp Arg Tyr Arg His Asn Tyr Leu His His
```

|  |  |  |  |  | 115 |  |  |  |  | 120 |  |  |  |  | 125 |
|---|---|---|---|---|---|---|---|---|---|---|---|---|---|---|---|
| Thr | Tyr 130 | Thr | Asn | Ile | Leu | Gly 135 | His | Asp | Val | Glu | Ile 140 | His | Gly | Asp | Gly |
| Ala 145 | Val | Arg | Met | Ser | Pro 150 | Glu | Gln | Glu | His | Val 155 | Gly | Ile | Tyr | Arg | Phe 160 |
| Gln | Gln | Phe | Tyr | Ile 165 | Trp | Gly | Leu | Tyr | Leu 170 | Phe | Ile | Pro | Phe 175 | Tyr | Trp |
| Phe | Leu | Tyr | Asp 180 | Val | Tyr | Leu | Val | Leu 185 | Asn | Lys | Gly | Lys 190 | Tyr | His | Asp |
| His | Lys | Ile 195 | Pro | Pro | Phe | Gln | Pro 200 | Leu | Glu | Leu | Ala | Ser 205 | Leu | Leu | Gly |
| Ile | Lys 210 | Leu | Leu | Trp | Leu | Gly 215 | Tyr | Val | Phe | Gly | Leu 220 | Pro | Leu | Ala | Leu |
| Gly 225 | Phe | Ser | Ile | Pro | Glu 230 | Val | Leu | Ile | Gly | Ala 235 | Ser | Val | Thr | Tyr | Met 240 |
| Thr | Tyr | Gly | Ile | Val 245 | Val | Cys | Thr | Ile | Phe 250 | Met | Leu | Ala | His | Val 255 | Leu |
| Glu | Ser | Thr | Glu 260 | Phe | Leu | Thr | Pro | Asp 265 | Gly | Glu | Ser | Gly | Ala 270 | Ile | Asp |
| Asp | Glu | Trp 275 | Ala | Ile | Cys | Gln | Ile 280 | Arg | Thr | Thr | Ala | Asn 285 | Phe | Ala | Thr |
| Asn | Asn 290 | Pro | Phe | Trp | Asn | Trp 295 | Phe | Cys | Gly | Gly | Leu 300 | Asn | His | Gln | Val |
| Thr 305 | His | His | Leu | Phe | Pro 310 | Asn | Ile | Cys | His | Ile 315 | His | Tyr | Pro | Gln | Leu 320 |
| Glu | Asn | Ile | Ile | Lys 325 | Asp | Val | Cys | Gln | Glu 330 | Phe | Gly | Val | Glu | Tyr 335 | Lys |
| Val | Tyr | Pro | Thr 340 | Phe | Lys | Ala | Ala | Ile 345 | Ala | Ser | Asn | Tyr | Arg 350 | Trp | Leu |
| Glu | Ala | Met | Gly 355 | Lys | Ala | Ser |  |  |  |  |  |  |  |  |  |

( 2 ) INFORMATION FOR SEQ ID NO:3:

( i ) SEQUENCE CHARACTERISTICS:
        ( A ) LENGTH: 1884 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:3:

```
AGCTTCACTT  CGGTTTTATA  TTGTGACCAT  GGTTCCCAGG  CATCTGCTCT  AGGGAGTTTT    60
TCCGCTGCCT  TTAGAGAGTA  TTTTCTCCAA  GTCGGCTAAC  TCCCCCATTT  TTAGGCAAAA   120
TCATATACAG  ACTATCCCAA  TATTGCCAGA  GCTTTGATGA  CTCACTGTAG  AAGGCAGACT   180
AAAATTCTAG  CAATGGACTC  CCAGTTGGAA  TAAATTTTTA  GTCTCCCCCG  GCGCTGGAGT   240
TTTTTTGTAG  TTAATGGCGG  TATAATGTGA  AAGTTTTTTA  TCTATTTAAA  TTTATAAATG   300
CTAACAGCGG  AAAGAATTAA  ATTTACCCAG  AAACGGGGGT  TCGTCGGGT   ACTAAACCAA   360
CGGGTGGATG  CCTACTTTGC  CGAGCATGGC  CTGACCCAAA  GGGATAATCC  CTCCATGTAT   420
CTGAAAACCC  TGATTATTGT  GCTCTGGTTG  TTTTCCGCTT  GGGCCTTTGT  GCTTTTTGCT   480
CCAGTTATTT  TTCCGGTGCG  CCTACTGGGT  TGTATGGTTT  TGGCGATCGC  CTTGGCGGCC   540
TTTTCCTTCA  ATGTCGGCCA  CGATGCCAAC  CACAATGCCT  ATTCCTCCAA  TCCCCACATC   600
```

-continued

| | | | | | |
|---|---|---|---|---|---|
|AACCGGGTTC|TGGGCATGAC|CTACGATTTT|GTCGGGTTAT|CTAGTTTTCT|TTGGCGCTAT|660|
|CGCCACAACT|ATTTGCACCA|CACCTACACC|AATATTCTTG|GCCATGACGT|GGAAATCCAT|720|
|GGAGATGGCG|CAGTACGTAT|GAGTCCTGAA|CAAGAACATG|TTGGTATTTA|TCGTTTCCAG|780|
|CAATTTTATA|TTTGGGGTTT|ATATCTTTTC|ATTCCCTTTT|ATTGGTTTCT|CTACGATGTC|840|
|TACCTAGTGC|TTAATAAAGG|CAAATATCAC|GACCATAAAA|TTCCTCCTTT|CCAGCCCCTA|900|
|GAATTAGCTA|GTTGCTAGG|GATTAAGCTA|TTATGGCTCG|GCTACGTTTT|CGGCTTACCT|960|
|CTGGCTCTGG|GCTTTTCCAT|TCCTGAAGTA|TTAATTGGTG|CTTCGGTAAC|CTATATGACC|1020|
|TATGGCATCG|TGGTTTGCAC|CATCTTTATG|CTGGCCCATG|TGTTGGAATC|AACTGAATTT|1080|
|CTCACCCCCG|ATGGTGAATC|CGGTGCCATT|GATGACGAGT|GGGCTATTTG|CCAAATTCGT|1140|
|ACCACGGCCA|ATTTGCCAC|CAATAATCCC|TTTGGAACT|GGTTTGTGG|CGGTTTAAAT|1200|
|CACCAAGTTA|CCCACCATCT|TTTCCCCAAT|ATTTGTCATA|TTCACTATCC|CCAATTGGAA|1260|
|AATATTATTA|AGGATGTTTG|CCAAGAGTTT|GGTGTGGAAT|ATAAAGTTTA|TCCCACCTTC|1320|
|AAAGCGGCGA|TCGCCTCTAA|CTATCGCTGG|CTAGAGGCCA|TGGGCAAAGC|ATCGTGACAT|1380|
|TGCCTTGGGA|TTGAAGCAAA|ATGGCAAAAT|CCCTCGTAAA|TCTATGATCG|AAGCCTTTCT|1440|
|GTTGCCCGCC|GACCAAATCC|CCGATGCTGA|CCAAAGGTTG|ATGTTGGCAT|TGCTCCAAAC|1500|
|CCACTTGAG|GGGGTTCATT|GGCCGCAGTT|TCAAGCTGAC|CTAGGAGGCA|AAGATTGGGT|1560|
|GATTTGCTC|AAATCCGCTG|GGATATTGAA|AGGCTTCACC|ACCTTTGGTT|TCTACCCTGC|1620|
|TCAATGGGAA|GGACAAACCG|TCAGAATTGT|TTATTCTGGT|GACACCATCA|CCGACCCATC|1680|
|CATGTGGTCT|AACCCAGCCC|TGGCCAAGGC|TTGGACCAAG|GCCATGCAAA|TTCTCCACGA|1740|
|GGCTAGGCCA|GAAAAATTAT|ATTGGCTCCT|GATTCTTCC|GGCTATCGCA|CCTACCGATT|1800|
|TTTGAGCATT|TTTGCCAAGG|AATTCTATCC|CCACTATCTC|CATCCCACTC|CCCCGCCTGT|1860|
|ACAAAATTTT|ATCCATCAGC|TAGC| | | |1884|

(2) INFORMATION FOR SEQ ID NO:4:

(i) SEQUENCE CHARACTERISTICS:
        (A) LENGTH: 1685 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:4:

| | | | | | |
|---|---|---|---|---|---|
|AATATCTGCC|TACCCTCCCA|AAGAGAGTAG|TCATTTTTCA|TCAATGGCTG|CTCAAATCAA|60|
|GAAATACATT|ACCTCAGATG|AACTCAAGAA|CCACGATAAA|CCCGGAGATC|TATGGATCTC|120|
|GATTCAAGGG|AAAGCCTATG|ATGTTTCGGA|TTGGGTGAAA|GACCATCCAG|GTGGCAGCTT|180|
|TCCCTTGAAG|AGTCTTGCTG|GTCAAGAGGT|AACTGATGCA|TTTGTTGCAT|TCCATCCTGC|240|
|CTCTACATGG|AAGAATCTTG|ATAAGTTTTT|CACTGGGTAT|TATCTTAAAG|ATTACTCTGT|300|
|TTCTGAGGTT|TCTAAAGATT|ATAGGAAGCT|TGTGTTTGAG|TTTTCTAAAA|TGGGTTTGTA|360|
|TGACAAAAAA|GGTCATATTA|TGTTTGCAAC|TTTGTGCTTT|ATAGCAATGC|TGTTTGCTAT|420|
|GAGTGTTTAT|GGGGTTTTGT|TTTGTGAGGG|TGTTTTGGTA|CATTTGTTTT|CTGGGTGTTT|480|
|GATGGGGTTT|CTTTGGATTC|AGAGTGGTTG|GATTGGACAT|GATGCTGGGC|ATTATATGGT|540|
|AGTGTCTGAT|TCAAGGCTTA|ATAAGTTTAT|GGGTATTTTT|GCTGCAAATT|GTCTTCAGG|600|
|AATAAGTATT|GGTTGGTGGA|AATGGAACCA|TAATGCACAT|CACATTGCCT|GTAATAGCCT|660|
|TGAATATGAC|CCTGATTTAC|AAATATATACC|ATTCCTTGTT|GTGTCTTCCA|AGTTTTTTGG|720|

-continued

```
TTCACTCACC TCTCATTTCT ATGAGAAAAG GTTGACTTTT GACTCTTTAT CAAGATTCTT        780
TGTAAGTTAT CAACATTGGA CATTTTACCC TATTATGTGT GCTGCTAGGC TCAATATGTA        840
TGTACAATCT CTCATAATGT TGTTGACCAA GAGAAATGTG TCCTATCGAG CTCAGGAACT        900
CTTGGGATGC CTAGTGTTCT CGATTTGGTA CCCGTTGCTT GTTTCTTGTT TGCCTAATTG        960
GGGTGAAAGA ATTATGTTTG TTATTGCAAG TTTATCAGTG ACTGGAATGC AACAAGTTCA       1020
GTTCTCCTTG AACCACTTCT CTTCAAGTGT TTATGTTGGA AAGCCTAAAG GGAATAATTG       1080
GTTTGAGAAA CAAACGGATG GGACACTTGA CATTTCTTGT CCTCCTTGGA TGGATTGGTT       1140
TCATGGTGGA TTGCAATTCC AAATTGAGCA TCATTTGTTT CCCAAGATGC CTAGATGCAA       1200
CCTTAGGAAA ATCTCGCCCT ACGTGATCGA GTTATGCAAG AAACATAATT TGCCTTACAA       1260
TTATGCATCT TTCTCCAAGG CCAATGAAAT GACACTCAGA ACATTGAGGA ACACAGCATT       1320
GCAGGCTAGG GATATAACCA AGCCGCTCCC GAAGAATTTG GTATGGGAAG CTCTTCACAC       1380
TCATGGTTAA AATTACCCTT AGTTCATGTA ATAATTTGAG ATTATGTATC TCCTATGTTT       1440
GTGTCTTGTC TTGGTTCTAC TTGTTGGAGT CATTGCAACT TGTCTTTTAT GGTTTATTAG       1500
ATGTTTTTTA ATATATTTTA GAGGTTTTGC TTTCATCTCC ATTATTGATG AATAAGGAGT       1560
TGCATATTGT CAATTGTTGT GCTCAATATC TGATATTTTG GAATGTACTT TGTACCACTG       1620
TGTTTCAGT TGAAGCTCAT GTGTACTTCT ATAGACTTTG TTTAAATGGT TATGTCATGT        1680
TATTT                                                                   1685
```

( 2 ) INFORMATION FOR SEQ ID NO:5:

( i ) SEQUENCE CHARACTERISTICS:
      ( A ) LENGTH: 448 amino acids
      ( B ) TYPE: amino acid
      ( D ) TOPOLOGY: linear ( i i ) MOLECULE TYPE:

( x i ) SEQUENCE DESCRIPTION: SEQ ID NO:5:

```
Met Ala Ala Gln Ile Lys Lys Tyr Ile Thr Ser Asp Glu Leu Lys Asn
 1               5                  10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175
```

-continued

| | | | | | | | | | | | | | |
|---|---|---|---|---|---|---|---|---|---|---|---|---|---|
|Gly|Ile|Phe|Ala 180|Ala|Asn|Cys|Leu|Ser 185|Gly|Ile|Ser|Ile|Gly 190|Trp|Trp|
|Lys|Trp|Asn 195|His|Asn|Ala|His|His 200|Ile|Ala|Cys|Asn|Ser 205|Leu|Glu|Tyr|
|Asp|Pro 210|Asp|Leu|Gln|Tyr|Ile 215|Pro|Phe|Leu|Val|Val 220|Ser|Ser|Lys|Phe|
|Phe 225|Gly|Ser|Leu|Thr|Ser 230|His|Phe|Tyr|Glu|Lys 235|Arg|Leu|Thr|Phe|Asp 240|
|Ser|Leu|Ser|Arg|Phe 245|Phe|Val|Ser|Tyr|Gln 250|His|Trp|Thr|Phe|Tyr 255|Pro|
|Ile|Met|Cys|Ala 260|Ala|Arg|Leu|Asn|Met 265|Tyr|Val|Gln|Ser|Leu 270|Ile|Met|
|Leu|Leu|Thr 275|Lys|Arg|Asn|Val|Ser 280|Tyr|Arg|Ala|Gln|Glu 285|Leu|Leu|Gly|
|Cys|Leu 290|Val|Phe|Ser|Ile|Trp 295|Tyr|Pro|Leu|Leu|Val 300|Ser|Cys|Leu|Pro|
|Asn 305|Trp|Gly|Glu|Arg|Ile 310|Met|Phe|Val|Ile|Ala 315|Ser|Leu|Ser|Val|Thr 320|
|Gly|Met|Gln|Gln|Val 325|Gln|Phe|Ser|Leu|Asn 330|His|Phe|Ser|Ser|Ser 335|Val|
|Tyr|Val|Gly|Lys 340|Pro|Lys|Gly|Asn|Asn 345|Trp|Phe|Glu|Lys|Gln 350|Thr|Asp|
|Gly|Thr|Leu 355|Asp|Ile|Ser|Cys|Pro 360|Pro|Trp|Met|Asp|Trp 365|Phe|His|Gly|
|Gly|Ser|Gln 370|Phe|Gln|Ile|Glu 375|His|His|Leu|Phe|Pro 380|Lys|Met|Pro|Arg|
|Cys 385|Asn|Leu|Arg|Lys|Ile 390|Ser|Pro|Tyr|Val|Ile 395|Glu|Leu|Cys|Lys|Lys 400|
|His|Asn|Leu|Pro|Tyr 405|Asn|Tyr|Ala|Ser|Phe 410|Ser|Lys|Ala|Asn|Glu 415|Met|
|Thr|Leu|Arg|Thr 420|Leu|Arg|Asn|Thr|Ala 425|Leu|Gln|Ala|Arg|Asp 430|Ile|Thr|
|Lys|Pro|Leu 435|Pro|Lys|Asn|Leu|Val 440|Trp|Glu|Ala|Leu|His 445|Thr|His|Gly|

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE:

( x i ) SEQUENCE DESCRIPTION: SEQ ID NO:6:

Trp Ile Gly His Asp Ala Gly His
  1             5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE:

( x i ) SEQUENCE DESCRIPTION: SEQ ID NO:7:

Asn Val Gly His Asp Ala Asn His
  1             5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE:

( x i ) SEQUENCE DESCRIPTION: SEQ ID NO:8:

Val Leu Gly His Asp Cys Gly His
    1                5

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE:

( x i ) SEQUENCE DESCRIPTION: SEQ ID NO:9:

Val Ile Ala His Glu Cys Gly His
    1                5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE:

( x i ) SEQUENCE DESCRIPTION: SEQ ID NO:10:

Val Ile Gly His Asp Cys Ala His
    1                5

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE:

( x i ) SEQUENCE DESCRIPTION: SEQ ID NO:11:

Val Val Gly His Asp Cys Gly His
    1                5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE:

( x i ) SEQUENCE DESCRIPTION: SEQ ID NO:12:

His Asn Ala His His
    1            5

( 2 ) INFORMATION FOR SEQ ID NO:13:

( i ) SEQUENCE CHARACTERISTICS:

(A) LENGTH: 6 amino acids
(B) TYPE: amino acid
(D) TOPOLOGY: linear (ii) MOLECULE TYPE:

(xi) SEQUENCE DESCRIPTION: SEQ ID NO:13:

His Asn Tyr Leu His His
1               5

(2) INFORMATION FOR SEQ ID NO:14:

(i) SEQUENCE CHARACTERISTICS:
(A) LENGTH: 5 amino acids
(B) TYPE: amino acid
(D) TOPOLOGY: linear (ii) MOLECULE TYPE:

(xi) SEQUENCE DESCRIPTION: SEQ ID NO:14:

His Arg Thr His His
1             5

(2) INFORMATION FOR SEQ ID NO:15:

(i) SEQUENCE CHARACTERISTICS:
(A) LENGTH: 5 amino acids
(B) TYPE: amino acid
(D) TOPOLOGY: linear (ii) MOLECULE TYPE:

(xi) SEQUENCE DESCRIPTION: SEQ ID NO:15:

His Arg Arg His His
1             5

(2) INFORMATION FOR SEQ ID NO:16:

(i) SEQUENCE CHARACTERISTICS:
(A) LENGTH: 5 amino acids
(B) TYPE: amino acid
(D) TOPOLOGY: linear (ii) MOLECULE TYPE:

(xi) SEQUENCE DESCRIPTION: SEQ ID NO:16:

His Asp Arg His His
1             5

(2) INFORMATION FOR SEQ ID NO:17:

(i) SEQUENCE CHARACTERISTICS:
(A) LENGTH: 5 amino acids
(B) TYPE: amino acid
(D) TOPOLOGY: linear (ii) MOLECULE TYPE:

(xi) SEQUENCE DESCRIPTION: SEQ ID NO:17:

His Asp Gln His His
1             5

(2) INFORMATION FOR SEQ ID NO:18:

(i) SEQUENCE CHARACTERISTICS:
(A) LENGTH: 5 amino acids
(B) TYPE: amino acid
(D) TOPOLOGY: linear (ii) MOLECULE TYPE:

( x i ) SEQUENCE DESCRIPTION: SEQ ID NO:18:

His Asp His His His
1                 5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE:

( x i ) SEQUENCE DESCRIPTION: SEQ ID NO:19:

His Asn His His His
1                 5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE:

( x i ) SEQUENCE DESCRIPTION: SEQ ID NO:20:

Phe Gln Ile Glu His His
1                 5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE:

( x i ) SEQUENCE DESCRIPTION: SEQ ID NO:21:

His Gln Val Thr His His
1                 5

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE:

( x i ) SEQUENCE DESCRIPTION: SEQ ID NO:22:

His Val Ile His His
1                 5

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE:

( x i ) SEQUENCE DESCRIPTION: SEQ ID NO:23:

His Val Ala His His
1                 5

(2) INFORMATION FOR SEQ ID NO:24:

(i) SEQUENCE CHARACTERISTICS:
　　　　(A) LENGTH: 5 amino acids
　　　　(B) TYPE: amino acid
　　　　(D) TOPOLOGY: linear (ii) MOLECULE TYPE:

(xi) SEQUENCE DESCRIPTION: SEQ ID NO:24:

His Ile Pro His His
　　1               5

(2) INFORMATION FOR SEQ ID NO:25:

(i) SEQUENCE CHARACTERISTICS:
　　　　(A) LENGTH: 5 amino acids
　　　　(B) TYPE: amino acid
　　　　(D) TOPOLOGY: linear (ii) MOLECULE TYPE:

(xi) SEQUENCE DESCRIPTION: SEQ ID NO:25:

His Val Pro His His
　　1               5

PRODUCTION OF γ-LINOLENIC ACID BY A Δ6-DESATURASE

This application is a continuation of application Ser. No. 08/366,779 filed Dec. 30, 1994 U.S. Pat. No. 5,614,393 which is a continuation-in-part of U.S. Ser. No. 08/307,382, filed Sep. 14, 1994, U.S. Pat. No. 5,552,306, which is a continuation of U.S. Ser. No. 07/959,952 filed Oct. 13, 1992 now abandoned, which is a continuation-in-part of U.S. Ser. No. 07/817,919, filed Jan. 8, 1992, now abandoned, which is a continuation-in-part application of U.S. Ser. No. 07/774,475 filed Oct. 10, 1991 now abandoned.

FIELD OF THE INVENTION

Linoleic acid (18:2) (LA) is transformed into gamma linolenic acid (18:3) (GLA) by the enzyme Δ6-desaturase. When this enzyme, or the nucleic acid encoding it, is transferred into LA-producing cells, GLA is produced. The present invention provides nucleic acids comprising the Δ6-desaturase gene. More specifically, the nucleic acids comprise the promoters, coding regions and termination regions of the Δ6-desaturase genes. The present invention is further directed to recombinant constructions comprising a Δ6-desaturase coding region in functional combination with heterologous regulatory sequences. The nucleic acids and recombinant constructions of the instant invention are useful in the production of GLA in transgenic organisms.

BACKGROUND OF THE INVENTION

Unsaturated fatty acids such as linoleic ($C_{18}\Delta^{9,12}$) and α-linolenic ($C_{18}\Delta^{9,12,15}$) acids are essential dietary constituents that cannot be synthesized by vertebrates since vertebrate cells can introduce double bonds at the $\Delta^9$ position of fatty acids but cannot introduce additional double bonds between the $\Delta^9$ double bond and the methyl-terminus of the fatty acid chain. Because they are precursors of other products, linoleic and α-linolenic acids are essential fatty acids, and are usually obtained from plant sources. Linoleic acid can be converted by mammals into γ-linolenic acid (GLA, $C_{18}\Delta^{6,9,12}$) which can in turn be converted to arachidonic acid (20:4), a critically important fatty acid since it is an essential precursor of most prostaglandins.

The dietary provision of linoleic acid, by virtue of its resulting conversion to GLA and arachidonic acid, satisfies the dietary need for GLA and arachidonic acid. However, a relationship has been demonstrated between consumption of saturated fats and health risks such as hypercholesterolemia, atherosclerosis and other clinical disorders which correlate with susceptibility to coronary disease, while the consumption of unsaturated fats has been associated with decreased blood cholesterol concentration and reduced risk of atherosclerosis. The therapeutic benefits of dietary GLA may result from GLA being a precursor to arachidonic acid and thus subsequently contributing to prostaglandin synthesis. Accordingly, consumption of the more unsaturated GLA, rather than linoleic acid, has potential health benefits. However, GLA is not present in virtually any commercially grown crop plant.

Linoleic acid is converted into GLA by the enzyme Δ6-desaturase. Δ6-desaturase, an enzyme of more than 350 amino acids, has a membrane-bound domain and an active site for desaturation of fatty acids. When this enzyme is transferred into cells which endogenously produce linoleic acid but not GLA, GLA is produced. The present invention, by providing the gene encoding Δ6-desaturase, allows the production of transgenic organisms which contain functional Δ6-desaturase and which produce GLA. In addition to allowing production of large amounts of GLA, the present invention provides new dietary sources of GLA.

SUMMARY OF THE INVENTION

The present invention is directed to isolated Δ6-desaturase genes. Specifically, the isolated genes comprises the Δ6-desaturase promoters, coding regions, and termination regions.

The present invention is further directed to expression vectors comprising the Δ6-desaturase promoter, coding region and termination region.

Yet another aspect of this invention is directed to expression vectors comprising a Δ6-desaturase coding region in functional combination with heterologous regulatory regions, i.e. elements not derived from the Δ6-desaturase gene.

Cells and organisms comprising the vectors of the present invention, and progeny of such organisms, are also provided by the present invention.

A further aspect of the present invention provides isolated bacterial Δ6-desaturase. An isolated plant Δ6-desaturase is also provided.

Yet another aspect of this invention provides a method for producing plants with increased gamma linolenic acid content.

A method for producing chilling tolerant plants is also provided by the present invention.

BRIEF DESCRIPTION OF THE DRAWINGS

FIG. 1 depicts the hydropathy profiles of the deduced amino acid sequences of Synechocystis Δ6-desaturase (Panel A) and Δ12-desaturase (Panel B). Putative membrane spanning regions are indicated by solid bars. Hydrophobic index was calculated for a window size of 19 amino acid residues [Kyte, et al. (1982) J. Molec. Biol. 157].

FIG. 4 provides gas liquid chromatography profiles of wild type (Panel A) and transgenic (Panel B) tobacco.

FIG. 5A depicts the DNA sequence of a Δ-6 desaturase cDNA isolated from borage.

FIG. 5B depicts the protein sequence of the open reading frame in the isolated borage Δ-6 desaturase cDNA. Three amino acid motifs characteristic of desaturases are indicated and are, in order, lipid box, metal box 1, and metal box 2.

FIG. 8 provides gas liquid chromatography profiles of mock transfected (Panel A) and 221.Δ6.NOS transfected (Panel B) carrot cells. The positions of 18:2, 18:3 α, and 18:3 γ(GLA) are indicated.

DETAILED DESCRIPTION OF THE INVENTION

Figure 2A:
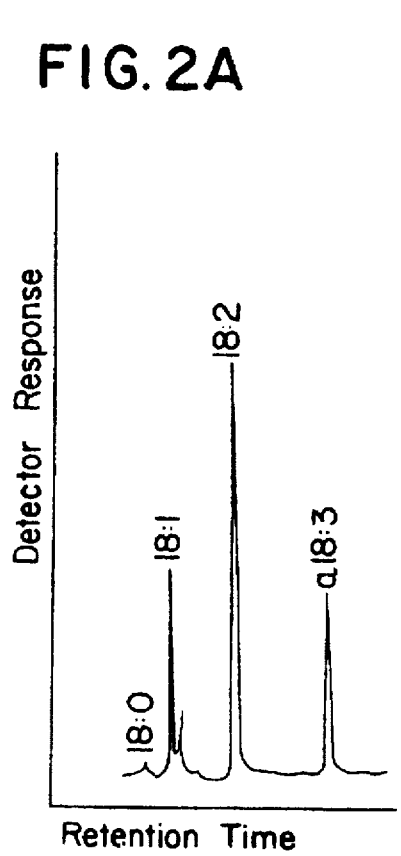
FIG. 2 provides gas liquid chromatography profiles of wild type (Panel A) and transgenic (Panel B) Anabaena.

The present invention provides isolated nucleic acids encoding Δ6-desaturase. To identify a nucleic acid encoding Δ6-desaturase, DNA is isolated from an organism which produces GLA. Said organism can be, for example, an animal cell, certain fungi (e.g. Mortierella), certain bacteria (e.g. Synechocystis) or certain plants (borage, Oenothera, currants). The isolation of genomic DNA can be accomplished by a variety of methods well-known to one of ordinary skill in the art, as exemplified by Sambrook et al. (1989) in *Molecular Cloning: A Laboratory Manual*, Cold Spring Harbor, N.Y. The isolated DNA is fragmented by physical methods or enzymatic digestion and cloned into an appropriate vector, e.g. a bacteriophage or cosmid vector, by any of a variety of well-known methods which can be found in references such as Sambrook et al. (1989). Expression vectors containing the DNA of the present invention are specifically contemplated herein. DNA encoding Δ6-desaturase can be identified by gain of function analysis. The vector containing fragmented DNA is transferred, for example by infection, transconjugation, transfection, into a host organism that produces linoleic acid but not GLA. As used herein, "transformation" refers generally to the incorporation of foreign DNA into a host cell. Methods for introducing recombinant DNA into a host organism are known to one of ordinary skill in the art and can be found, for example, in Sambrook et al. (1989). Production of GLA by these organisms (i.e., gain of function) is assayed, for example by gas chromatography or other methods known to the ordinarily skilled artisan. Organisms which are induced to produce GLA, i.e. have gained function by the introduction of the vector, are identified as expressing DNA encoding Δ6-desaturase, and said DNA is recovered from the organisms. The recovered DNA can again be fragmented, cloned with expression vectors, and functionally assessed by the above procedures to define with more particularity the DNA encoding Δ6-desaturase.

As an example of the present invention, random DNA is isolated from the cyanobacteria Synechocystis Pasteur Culture Collection (PCC) 6803, American Type Culture Collection (ATCC) 27184, cloned into a cosmid vector, and introduced by transconjugation into the GLA-deficient cyanobacterium Anabaena strain PCC 7120, ATCC 27893. Production of GLA from Anabaena linoleic acid is monitored by gas chromatography and the corresponding DNA fragment is isolated.

The isolated DNA is sequenced by methods well-known to one of ordinary skill in the art as found, for example, in Sambrook et al. (1989).

In accordance with the present invention, DNA molecules comprising Δ6-desaturase genes have been isolated. More particularly, a 3.588 kilobase (kb) DNA comprising a Δ6-desaturase gene has been isolated from the cyanobacteria Synechocystis. The nucleotide sequence of the 3.588 kb DNA was determined and is shown in SEQ ID NO:1. Open reading frames defining potential coding regions are present from nucleotide 317 to 1507 and from nucleotide 2002 to 3081. To define the nucleotides responsible for encoding Δ6-desaturase, the 3.588 kb fragment that confers Δ6-desaturase activity is cleaved into two subfragments, each of which contains only one open reading frame. Fragment ORF1 contains nucleotides 1 through 1704, while fragment ORF2 contains nucleotides 1705 through 3588. Each fragment is subcloned in both forward and reverse orientations into a conjugal expression vector (AM542, Wolk et al. [1984] *Proc. Natl. Acad. Sci. USA* 81, 1561) that contains a cyanobacterial carboxylase promoter. The resulting constructs (i.e. ORF1(F), ORF1(R), ORF2(F) and ORF2 (R)] are conjugated to wild-type Anabaena PCC 7120 by standard methods (see, for example, Wolk et al. (1984) *Proc. Natl. Acad. Sci. USA* 81, 1561). Conjugated cells of Anabaena are identified as Neo$^R$ green colonies on a brown background of dying non-conjugated cells after two weeks of growth on selective media (standard mineral media BG11N+ containing 30 µg/ml of neomycin according to Rippka et al., (1979) *J. Gen Microbiol.* 111, 1). The green colonies are selected and grown in selective liquid media (BG11N+ with 15 µg/ml neomycin). Lipids are extracted by standard methods (e.g. Dahmer et al., (1989) *Journal of American Oil Chemical Society* 66, 543) from the resulting transconjugants containing the forward and reverse oriented ORF1 and ORF2 constructs. For comparison, lipids are also extracted from wild-type cultures of Anabaena and Synechocystis. The fatty acid methyl esters are analyzed by gas liquid chromatography (GLC), for example with a Tracor-560 gas liquid chromatograph equipped with a hydrogen flame ionization detector and a capillary column. The results of GLC analysis are shown in Table 1.

TABLE 1

| Occurrence of C18 fatty acids in wild-type and transgenic cyanobacteria | | | | | | |
|---|---|---|---|---|---|---|
| SOURCE | 18:0 | 18:1 | 18:2 | γ18:3 | α18:3 | 18:4 |
| Anabaena (wild type) | + | + | + | − | + | − |
| Anabaena + ORF1 (F) | + | + | + | − | + | − |
| Anabaena + ORF1 (R) | + | + | + | − | + | − |
| Anabaena + ORF2 (F) | + | + | + | + | + | + |
| Anabaena + ORF2 (R) | + | + | + | − | + | − |
| Synechocystis (wild type) | + | + | + | + | − | − |

As assessed by GLC analysis, GLA deficient Anabaena gain the function of GLA production when the construct containing ORF2 in forward orientation is introduced by transconjugation. Transconjugants containing constructs with ORF2 in reverse orientation to the carboxylase promoter, or ORF1 in either orientation, show no GLA production. This analysis demonstrates that the single open reading frame (ORF2) within the 1884 bp fragment encodes Δ6-desaturase. The 1884 bp fragment is shown as SEQ ID NO:3. This is substantiated by the overall similarity of the hydropathy profiles between Δ6-desaturase and Δ12-desaturase [Wada et al. (1990) *Nature* 347] as shown in FIG. 1 as (A) and (B), respectively.

Also in accordance with the present invention, a cDNA comprising a Δ6-desaturase gene from borage (*Borago officinalis*) has been isolated. The nucleotide sequence of the 1.685 kilobase (kb) cDNA was determined and is shown in FIG. 5A (SEQ ID NO: 4). The ATG start codon and stop codon are underlined. The amino acid sequence corresponding to the open reading frame in the borage delta 6-desaturase is shown in FIG. 5B (SEQ ID NO: 5).

Isolated nucleic acids encoding Δ6-desaturase can be identified from other GLA-producing organisms by the gain of function analysis described above, or by nucleic acid hybridization techniques using the isolated nucleic acid which encodes Synechocystis or borage Δ6-desaturase as a hybridization probe. Both genomic and cDNA cloning methods are known to the skilled artisan and are contemplated by the present invention. The hybridization probe can comprise the entire DNA sequence disclosed as SEQ. ID NO:1 or SEQ. ID NO:4, or a restriction fragment or other DNA fragment thereof, including an oligonucleotide probe. Methods for cloning homologous genes by cross-hybridization are known to the ordinarily skilled artisan and can be found, for example, in Sambrook (1989) and Beltz et al. (1983) *Methods in Enzymology* 100, 266.

In another method of identifying a delta 6-desaturase gene from an organism producing GLA, a cDNA library is made from poly-A$^+$ RNA isolated from polysomal RNA. In order to eliminate hyper-abundant expressed genes from the cDNA population, cDNAs or fragments thereof corresponding to hyper-abundant cDNAs genes are used as hybridization probes to the cDNA library. Non hybridizing plaques are excised and the resulting bacterial colonies are used to inoculate liquid cultures and sequenced. For example, as a means of eliminating other seed storage protein cDNAs from a cDNA library made from borage polysomal RNA, cDNAs corresponding to abundantly expressed seed storage proteins are first hybridized to the cDNA library. The "subtracted" DNA library is then used to generate expressed sequence tags (ETSs) and such tags are used to scan a data base such as GenBank to identify potential desaturates.

Transgenic organisms which gain the function of GLA production by introduction of DNA encoding Δ-desaturase also gain the function of octadecatetraeonic acid (18:4Δ$^{6,9,12,15}$) production. Octadecatetraeonic acid is present normally in fish oils and in some plant species of the Boraginaceae family (Craig et al. [1964] *J. Amer. Oil Chem. Soc.* 41, 209–211; Gross et al. [1976] *Can. J. Plant Sci.* 56, 659–664). In the transgenic organisms of the present invention, octadecatetraenoic acid results from further desaturation of α-linolenic acid by Δ6-desaturase or desaturation of GLA by Δ15-desaturase.

The 359 amino acids encoded by ORF2, i.e. the open reading frame encoding Synechocystis Δ6-desaturase, are shown as SEQ. ID NO:2. The open reading frame encoding the borage Δ6-desaturase is shown in SEQ ID NO: 5. The present invention further contemplates other nucleotide sequences which encode the amino acids of SEQ ID NO:2 and SEQ ID NO: 5. It is within the ken of the ordinarily skilled artisan to identify such sequences which result, for example, from the degeneracy of the genetic code. Furthermore, one of ordinary skill in the art can determine, by the gain of function analysis described hereinabove, smaller subfragments of the fragments containing the open reading frames which encode Δ6-desaturases.

The present invention contemplates any such polypeptide fragment of Δ6-desaturase and the nucleic acids therefor which retain activity for converting LA to GLA.

In another aspect of the present invention, a vector containing a nucleic acid of the present invention or a smaller fragment containing the promoter, coding sequence and termination region of a Δ6-desaturase gene is transferred into an organism, for example, cyanobacteria, in which the Δ6-desaturase promoter and termination regions are functional. Accordingly, organisms producing recombinant Δ6-desaturase are provided by this invention. Yet another aspect of this invention provides isolated Δ6-desaturase, which can be purified from the recombinant organisms by standard methods of protein purification. (For example, see Ausubel et al. [1987] *Current Protocols in Molecular Biology*, Green Publishing Associates, New York).

Vectors containing DNA encoding Δ6-desaturase are also provided by the present invention. It will be apparent to one of ordinary skill in the art that appropriate vectors can be constructed to direct the expression of the Δ6-desaturase coding sequence in a variety of organisms. Replicable expression vectors are particularly preferred. Replicable expression vectors as described herein are DNA or RNA molecules engineered for controlled expression of a desired gene, i.e. the Δ6-desaturase gene. Preferably the vectors are plasmids, bacteriophages, cosmids or viruses. Shuttle vectors, e.g. as described by Wolk et al. (1984) *Proc. Natl. Acad. Sci. USA*, 1561–1565 and Bustos et al. (1991) *J. Bacteriol.* 174, 7525–7533, are also contemplated in accordance with the present invention. Sambrook et al. (1989), Goeddel, ed. (1990) *Methods in Enzymology* 185 Academic Press, and Perbal (1988) *A Practical Guide to Molecular Cloning*, John Wiley and Sons, Inc., provide detailed reviews of vectors into which a nucleic acid encoding the present Δ6-desaturase can be inserted and expressed. Such vectors also contain nucleic acid sequences which can effect expression of nucleic acids encoding Δ6-desaturase. Sequence elements capable of effecting expression of a gene product include promoters, enhancer elements, upstream activating sequences, transcription termination signals and polyadenylation sites. Both constitutive and tissue specific promoters are contemplated. For transformation of plant cells, the cauliflower mosaic virus (CaMV) 35S promoter and promoters which are regulated during plant seed maturation are of particular interest. All such promoter and transcriptional regulatory elements, singly or in combination, are contemplated for use in the present replicable expression vectors and are known to one of ordinary skill in the art. The CaMV 35S promoter is described, for example, by Restrepo et al. (1990) *Plant Cell* 2, 987. Genetically engineered and mutated regulatory sequences are also contemplated.

The ordinarily skilled artisan can determine vectors and regulatory elements suitable for expression in a particular host cell. For example, a vector comprising the promoter from the gene encoding the carboxylase of Anabaena operably linked to the coding region of Δ6-desaturase and further operably linked to a termination signal from Synechocystis is appropriate for expression of Δ6-desaturase in cyanobacteria. "Operably linked" in this context means that the promoter and terminator sequences effectively function to regulate transcription. As a further example, a vector appropriate for expression of Δ6-desaturase in transgenic plants can comprise a seed-specific promoter sequence derived from helianthinin, napin, or glycinin operably linked to the Δ6-desaturase coding region and further operably linked to a seed termination signal or the nopaline synthase termination signal. As a still further example, a vector for use in expression of Δ 6-desaturase in plants can comprise a constitutive promoter or a tissue specific promoter operably linked to the Δ 6-desaturase coding region and further operably linked to a constitutive or tissue specific terminator or the nopaline synthase termination signal.

In particular, the helianthinin regulatory elements disclosed in applicant's copending U.S. application Ser. No. 682,354, filed Apr. 8, 1991 and incorporated herein by reference, are contemplated as promoter elements to direct the expression of the Δ6-desaturase of the present invention.

Modifications of the nucleotide sequences or regulatory elements disclosed herein which maintain the functions contemplated herein are within the scope of this invention.

Such modifications include insertions, substitutions and deletions, and specifically substitutions which reflect the degeneracy of the genetic code.

Standard techniques for the construction of such hybrid vectors are well-known to those of ordinary skill in the art and can be found in references such as Sambrook et al. (1989), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in the hybrid vectors other nucleotide sequence elements which facilitate cloning, expression or processing, for example sequences encoding signal peptides, a sequence encoding KDEL, which is required for retention of proteins in the endoplasmic reticulum or sequences encoding transit peptides which direct Δ6-desaturase to the chloroplast. Such sequences are known to one of ordinary skill in the art. An optimized transit peptide is described, for example, by Van den Broeck et al. (1985) *Nature* 313, 358. Prokaryotic and eukaryotic signal sequences are disclosed, for example, by Michaelis et al. (1982) *Ann. Rev. Microbiol.* 36, 425.

A further aspect of the instant invention provides organisms other than cyanobacteria or plants which contain the DNA encoding the Δ6-desaturase of the present invention. The transgenic organisms contemplated in accordance with the present invention include bacteria, cyanobacteria, fungi, and plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989).

A variety of plant transformation methods are known. The Δ6-desaturase gene can be introduced into plants by a leaf disk transformation-regeneration procedure as described by Horsch et al. (1985) *Science* 227, 1229. Other methods of transformation, such as protoplast culture (Horsch et al. (1984) *Science* 223, 496; DeBlock et al. (1984) *EMBO J.* 2, 2143; Barton et al. (1983) *Cell* 32, 1033) can also be used and are within the scope of this invention. In a preferred embodiment plants are transformed with Agrobacterium-derived vectors. However, other methods are available to insert the Δ6-desaturase genes of the present invention into plant cells. Such alternative methods include biolistic approaches (Klein et al. (1987) *Nature* 327, 70), electroporation, chemically-induced DNA uptake, and use of viruses or pollen as vectors.

When necessary for the transformation method, the Δ6-desaturase genes of the present invention can be inserted into a plant transformation vector, e.g. the binary vector described by Bevan (1984) *Nucleic Acids Res.* 12, 8111. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

Surface-sterilized leaf disks are inoculated with the "disarmed" foreign DNA-containing *A. tumefaciens*, cultured for two days, and then transferred to antibiotic-containing medium. Transformed shoots are selected after rooting in medium containing the appropriate antibiotic, transferred to soil and regenerated.

Another aspect of the present invention provides transgenic plants or progeny of these plants containing the isolated DNA of the invention. Both monocotyledenous and dicotyledenous plants are contemplated. Plant cells are transformed with the isolated DNA encoding Δ6-desaturase by any of the plant transformation methods described above. The transformed plant cell, usually in a callus culture or leaf disk, is regenerated into a complete transgenic plant by methods well-known to one of ordinary skill in the art (e.g. Horsch et al. (1985) *Science* 227, 1129). In a preferred embodiment, the transgenic plant is sunflower, oil seed rape, maize, tobacco, peanut or soybean. Since progeny of transformed plants inherit the DNA encoding Δ6-desaturase, seeds or cuttings from transformed plants are used to maintain the transgenic plant line.

The present invention further provides a method for providing transgenic plants with an increased content of GLA. This method includes introducing DNA encoding Δ6-desaturase into plant cells which lack or have low levels of GLA but contain LA, and regenerating plants with increased GLA content from the transgenic cells. In particular, commercially grown crop plants are contemplated as the transgenic organism, including, but not limited to, sunflower, soybean, oil seed rape, maize, peanut and tobacco.

The present invention further provides a method for providing transgenic organisms which contain GLA. This method comprises introducing DNA encoding Δ6-desaturase into an organism which lacks or has low levels of GLA, but contains LA. In another embodiment, the method comprises introducing one or more expression vectors which comprise DNA encoding Δ12-desaturase and Δ6-desaturase into organisms which are deficient in both GLA and LA. Accordingly, organisms deficient in both LA and GLA are induced to produce LA by the expression of Δ12-desaturase, and GLA is then generated due to the expression of Δ6-desaturase. Expression vectors comprising DNA encoding Δ12-desaturase, or Δ12 -desaturase and Δ6-desaturase, can be constructed by methods of recombinant technology known to one of ordinary skill in the art (Sambrook et al., 1989) and the published sequence of Δ12-desaturase (Wada et al [1990] *Nature* (London) 347, 200–203. In addition, it has been discovered in accordance with the present invention that nucleotides 2002–3081 of SEQ. ID NO:1 encode cyanobacterial Δ12-desaturase. Accordingly, this sequence can be used to construct the subject expression vectors. In particular, commercially grown crop plants are contemplated as the transgenic organism, including, but not limited to, sunflower, soybean, oil seed rape, maize, peanut and tobacco.

The present invention is further directed to a method of inducing chilling tolerance in plants. Chilling sensitivity may be due to phase transition of lipids in cell membranes. Phase transition temperature depends upon the degree of unsaturation of fatty acids in membrane lipids, and thus increasing the degree of unsaturation, for example by introducing Δ6-desaturase to convert LA to GLA, can induce or improve chilling resistance. Accordingly, the present method comprises introducing DNA encoding Δ6-desaturase into a plant cell, and regenerating a plant with improved chilling resistance from said transformed plant cell. In a preferred embodiment, the plant is a sunflower, soybean, oil seed rape, maize, peanut or tobacco plant.

The following examples further illustrate the present invention.

EXAMPLE 1

Strains and Culture Conditions

Synechocystis (PCC 6803, ATCC 27184) Anabaena (PCC 7120, ATCC 27893) and Synechococcus (PCC 7942, ATCC 33912) were grown photoautotrophically at 30° C. in BG11N+ medium (Rippka et al. [1979] *J. Gen. Microbiol.* 111, 1–61) under illumination of incandescent lamps (60 µE.m$^{-2}$.S$^{-1}$). Cosmids and plasmids were selected and propagated in *Escherichia coli* strain DH5α on LB medium supplemented with antibiotics at standard concentrations as described by Maniatis et al. (1982) *Molecular Cloning: A Laboratory Manual*, Cold Spring Harbor Laboratory, Cold Spring, N.Y.

EXAMPLE 2

Construction of Synechocystis Cosmid Genomic Library

Total genomic DNA from Synechocystis (PCC 6803) was partially digested with Sau3A and fractionated on a sucrose gradient (Ausubel et al. [1987] *Current Protocols in Molecular Biology*, Greene Publishing Associates and Wiley Interscience, New York). Fractions containing 30 to 40 kb DNA fragments were selected and ligated into the dephosphorylated BamHI site of the cosmid vector, pDUCA7 (Buikema et al. [1991] *J. Bacteriol.* 173, 1879–1885). The ligated DNA was packaged in vitro as described by Ausubel et al. (1987), and packaged phage were propagated in *E. coli* DH5α containing the AvaI and Eco4711 methylase helper plasmid, pRL528 as described by Buikema et al. (1991). A total of 1152 colonies were isolated randomly and maintained individually in twelve 96-well microtiter plates.

EXAMPLE 3

Gain-of-Function Expression of GLA in Anabaena

Anabaena (PCC 7120), a filamentous cyanobacterium, is deficient in GLA but contains significant amounts of linoleic acid, the precursor for GLA (FIG. 2; Table 2). The Synechocystis cosmid library described in Example 2 was conjugated into Anabaena (PCC 7120) to identify transconjugants that produce GLA. Anabaena cells were grown to mid-log phase in BG11N+ liquid medium and resuspended in the same medium to a final concentration of approximately 2×10$^8$ cells per ml. A mid-log phase culture of *E. coli* RP4 (Burkardt et al. [1979] *J. Gen. Microbiol.* 114, 341–348) grown in LB containing ampicillin was washed and resuspended in fresh LB medium. Anabaena and RP4 were then mixed and spread evenly on BG11N+ plates containing 5% LB. The cosmid genomic library was replica plated onto LB plates containing 50 µg/ml kanamycin and 17.5 µg/ml chloramphenicol and was subsequently patched onto BG11N+ plates containing Anabaena and RP4. After 24 hours of incubation at 30° C., 30 µg/ml of neomycin was underlaid; and incubation at 30° C. was continued until transconjugants appeared.

Individual transconjugants were isolated after conjugation and grown in 2 ml BG11N+ liquid medium with 15 µg/ml neomycin. Fatty acid methyl esters were prepared from wild type cultures and cultures containing pools of ten transconjugants as follows. Wild type and transgenic cyanobacterial cultures were harvested by centrifugation and washed twice with distilled water. Fatty acid methyl esters were extracted from these cultures as described by Dahmer et al. (1989) *J. Amer. Oil. Chem. Soc.* 66, 543–548 and were analyzed by Gas Liquid Chromatography (GLC) using a Tracor-560 equipped with a hydrogen flame ionization detector and capillary column (30 m×0.25 mm bonded FSOT Superox II, Alltech Associates Inc., Ill.). Retention times and co-chromatography of standards (obtained from Sigma Chemical Co.) were used for identification of fatty acids. The average fatty acid composition was determined as the ratio of peak area of each C18 fatty acid normalized to an internal standard.

Representative GLC profiles are shown in FIG. 2. C18 fatty acid methyl esters are shown. Peaks were identified by comparing the elution times with known standards of fatty acid methyl esters and were confirmed by gas chromatography-mass spectrometry. Panel A depicts GLC analysis of fatty acids of wild type Anabaena. The arrow indicates the migration time of GLA. Panel B is a GLC profile of fatty acids of transconjugants of Anabaena with pAM542+1.8F. Two GLA producing pools (of 25 pools representing 250 transconjugants) were identified that produced GLA. Individual transconjugants of each GLA positive pool were analyzed for GLA production; two independent transconjugants, AS13 and AS75, one from each pool, were identified which expressed significant levels of GLA and which contained cosmids, cSy13 and cSy75, respectively (FIG. 3). The cosmids overlap in a region approximately 7.5 kb in length. A 3.5 kb NheI fragment of cSy75 was recloned in the vector pDUCA7 and transferred to Anabaena resulting in gain-of-function expression of GLA (Table 2).

Two NheI/Hind III subfragments (1.8 and 1.7 kb) of the 3.5 kb Nhe I fragment of cSy75-3.5 were subcloned into "pBLUESCRIPT" (Stratagene) (FIG. 3) for sequencing. Standard molecular biology techniques were performed as described by Maniatis et al. (1982) and Ausubel et al. (1987). Dideoxy sequencing (Sanger et al. [1977] *Proc. Natl. Acad. Sci. USA* 74, 5463–5467) of pBS1.8 was performed with "SEQUENASE" (United States Biochemical) on both strands by using specific oligonucleotide primers synthesized by the Advanced DNA Technologies Laboratory (Biology Department, Texas A & M University). DNA sequence analysis was done with the GCG (Madison, Wis.) software as described by Devereux et al. (1984) *Nucleic Acids Res.* 12, 387–395.

Both NheI/HindIII subfragments were transferred into a conjugal expression vector, AM542, in both forward and reverse orientations with respect to a cyanobacterial carboxylase promoter and were introduced into Anabaena by conjugation. Transconjugants containing the 1.8 kb fragment in the forward orientation (AM542-1.8F) produced significant quantities of GLA and octadecatetraenoic acid (FIG. 2; Table 2). Transconjugants containing other constructs, either reverse oriented 1.8 kb fragment or forward and reverse oriented 1.7 kb fragment, did not produce detectable levels of GLA (Table 2).

Figure 2B:
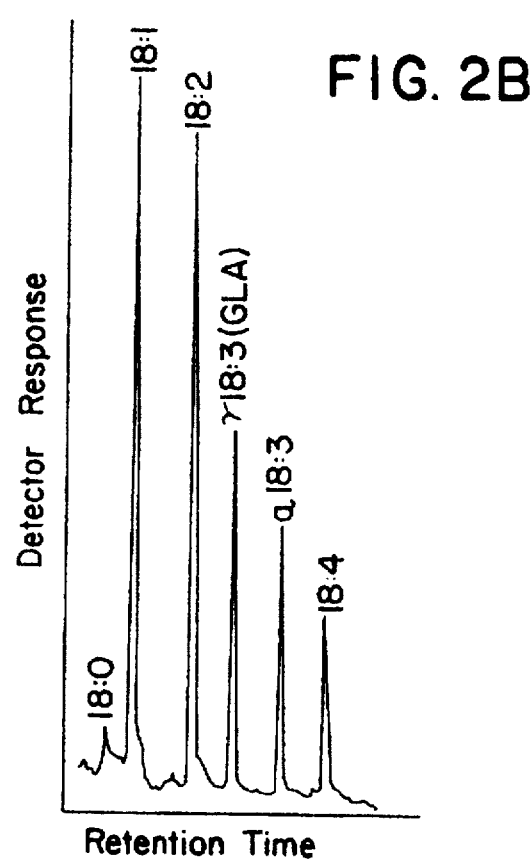
Figure 3:
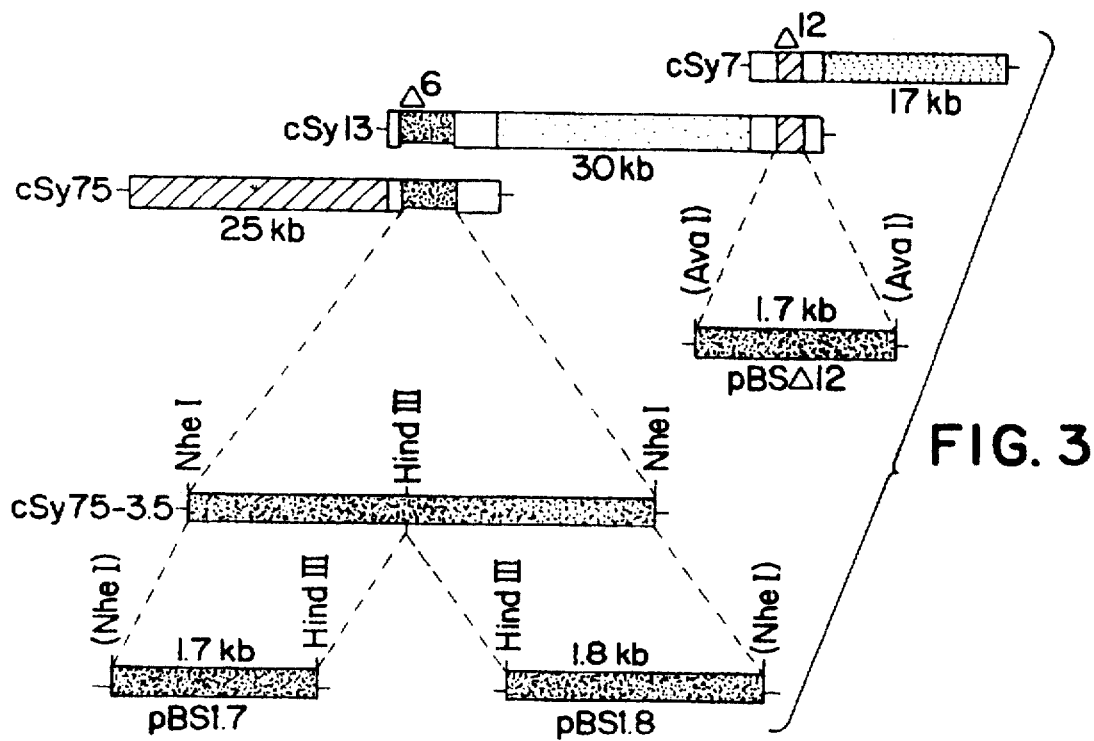
FIG. 3 is a diagram of maps of cosmid cSy75, cSy13 and Csy7 with overlapping regions and subclones. The origins of subclones of Csy75, Csy75-3.5 and Csy7 are indicated by the dashed diagonal lines. Restriction sites that have been inactivated are in parentheses.

FIG. 2 compares the C18 fatty acid profile of an extract from wild type Anabaena (FIG. 2A) with that of transgenic Anabaena containing the 1.8 kb fragment of cSy75-3.5 in the forward orientation (FIG. 2B). GLC analysis of fatty acid methyl esters from AM542-1.8F revealed a peak with a retention time identical to that of authentic GLA standard.

Analysis of this peak by gas chromatography-mass spectrometry (GC-MS) confirmed that it had the same mass fragmentation pattern as a GLA reference sample. Transgenic Anabaena with altered levels of polyunsaturated fatty acids were similar to wild type in growth rate and morphology.

Synechococcus containing both Δ12- and Δ6-desaturase genes has gained the capability of introducing a second double bond at the Δ12 position and a third double bond at the Δ6 position of C18 fatty acids. However, no changes in fatty acid composition was observed in the transformant containing pAM854-Δ6, indicating that in the absence of

TABLE 2

Composition of C18 Fatty Acids in Wild Type and Transgenic Cyanobacteria

| Strain | 18:0 | 18:1 | 18:2 | 18:3(α) | 18:3(γ) | 18:4 |
|---|---|---|---|---|---|---|
| Wild type | | | | | | |
| Synechocystis (sp. PCC6803) | 13.6 | 4.5 | 54.5 | — | 27.3 | — |
| Anabaena (sp. PCC7180) | 2.9 | 24.8 | 37.1 | 35.2 | — | — |
| Synechococcus (sp. PCC7942) | 20.6 | 79.4 | — | — | — | — |
| Anabaena Transconjugants | | | | | | |
| cSy75 | 3.8 | 24.4 | 22.3 | 9.1 | 27.9 | 12.5 |
| cSy75-3.5 | 4.3 | 27.6 | 18.1 | 3.2 | 40.4 | 6.4 |
| pAM542-1.8F | 4.2 | 13.9 | 12.1 | 19.1 | 25.4 | 25.4 |
| pAM542-1.8R | 7.7 | 23.1 | 38.4 | 30.8 | — | — |
| pAM542-1.7F | 2.8 | 27.8 | 36.1 | 33.3 | — | — |
| pAM542-1.7R | 2.8 | 25.4 | 42.3 | 29.6 | — | — |
| Synechococcus Transformants | | | | | | |
| pAM854 | 27.8 | 72.2 | — | — | — | — |
| pAM854-Δ$^{12}$ | 4.0 | 43.2 | 46.0 | — | — | — |
| pAM854-Δ$^{6}$ | 18.2 | 81.8 | — | — | — | — |
| pAM854-Δ$^{6}$ & Δ$^{12}$ | 42.7 | 25.3 | 19.5 | — | 16.5 | — |

18:0, stearic acid; 18:1, oleic acid; 18:2, linoleic acid; 18:3(α), α-linolenic acid; 18:3(γ), γ-linolenic acid; 18:4, octadecatetraenoic acid

EXAMPLE 4

Transformation of Synechococcus with Δ6 and Δ12 Desaturase Genes

A third cosmid, cSy7, which contains a Δ12-desaturase gene, was isolated by screening the Synechocystis genomic library with a oligonucleotide synthesized from the published Synechocystis Δ12-desaturase gene sequence (Wada et al. [1990] *Nature* (London) 347, 200–203). A 1.7 kb AvaI fragment from this cosmid containing the Δ12-desaturase gene was identified and used as a probe to demonstrate that cSy13 not only contains a Δ6-desaturase gene but also a Δ12-desaturase gene (FIG. 3). Genomic Southern blot analysis further showed that both the Δ6-and Δ12-desaturase genes are unique in the Synechocystis genome so that both functional genes involved in C18 fatty acid desaturation are linked closely in the Synechocystis genome.

The unicellular cyanobacterium Synechococcus (PCC 7942) is deficient in both linoleic acid and GLA(3). The Δ12 and Δ6-desaturase genes were cloned individually and together into pAM854 (Bustos et al. [1991] *J. Bacteriol.* 174, 7525–7533), a shuttle vector that contains sequences necessary for the integration of foreign DNA into the genome of Synechococcus (Golden et al. [1987] *Methods in Enzymol.* 153, 215–231). Synechococcus was transformed with these gene constructs and colonies were selected. Fatty acid methyl esters were extracted from transgenic Synechococcus and analyzed by GLC.

Table 2 shows that the principal fatty acids of wild type Synechococcus are stearic acid (18:0) and oleic acid (18:1). Synechococcus transformed with pAM854-Δ12 expressed linoleic acid (18:2) in addition to the principal fatty acids. Transformants with pAM854-Δ6 and Δ12 produced both linoleate and GLA (Table 1). These results indicated that substrate synthesized by the Δ12 desaturase, the Δ6-desaturase is inactive. This experiment further confirms that the 1.8 kb NheI/HindIII fragment (FIG. 3) contains both coding and promoter regions of the Synechocystis 66 6-desaturase gene. Transgenic Synechococcus with altered levels of polyunsaturated fatty acids were similar to wild type in growth rate and morphology.

EXAMPLE 5

Nucleotide Sequence of Δ6-Desaturase

The nucleotide sequence of the 1.8 kb fragment of cSy75-3.5 including the functional Δ6-desaturase gene was determined. An open reading frame encoding a polypeptide of 359 amino acids was identified (FIG. 4). A Kyte-Doolittle hydropathy analysis (Kyte et al. [1982] *J. Mol. Biol.* 157, 105–132) identified two regions of hydrophobic amino acids that could represent transmembrane domains (FIG. 1A); furthermore, the hydropathic profile of the Δ6-desaturase is similar to that of the Δ12-desaturase gene (FIG. 1B; Wada et al.) and Δ9-desaturases (Thiede et al. [1986] *J. Biol. Chem.* 261, 13230–13235). However, the sequence similarity between the Synechocystis Δ6- and Δ12-desaturases is less than 40% at the nucleotide level and approximately 18% at the amino acid level.

EXAMPLE 6

Transfer of Cyanobacterial Δ$^6$-Desaturase into Tobacco

The cyanobacterial Δ$^6$-desaturase gene was mobilized into a plant expression vector and transferred to tobacco using Agrobacterium mediated gene transfer techniques. To ensure that the transferred desaturase is appropriately expressed in leaves and developing seeds and that the desaturase gene product is targeted to the endoplasmic reticulum or the chloroplast, various expression cassettes with Synechocystis Δ-desaturase open reading frame (ORF) were constructed. Components of these cassettes include: (i) a 35S promoter or seed specific promoter derived from the sunflower helianthinin gene to drive $\Delta^6$-desaturase gene expression in all plant tissues or only in developing seeds respectively, (ii) a putative signal peptide either from carrot extensin gene or sunflower helianthinin gene to target newly synthesized $\Delta^6$-desaturase into the ER. (iii) an ER lumen retention signal sequence (KDEL) at the COOH-terminal of the $\Delta^6$-desaturase ORF, and (iv) an optimized transit peptide to target Δ6 desaturase into the chloroplast. The 35S promoter is a derivative of pRTL2 described by Restrepo et al. (1990). The optimized transit peptide sequence is described by Van de Broeck et al. (1985). The carrot extensin signal peptide is described by Chen et al (1985) *EMBO J.* 9, 2145.

Transgenic tobacco plants were produced containing a chimeric cyanobacterial desaturase gene, comprised of the Synechocystis $\Delta^6$ desaturase gene fused to an endoplasmic reticulum retention sequence (KDEL) and extensin signal peptide driven by the CaMV 35S promoter. PCR amplifications of transgenic tobacco genomic DNA indicate that the $\Delta^6$ desaturase gene was incorporated into the tobacco genome. Fatty acid methyl esters of leaves of these transgenic tobacco plants were extracted and analyzed by Gas Liquid Chromatography (GLC). These transgenic tobacco accumulated significant amounts of GLA (FIG. 4). FIG. 4 shows fatty acid methyl esters as determined by GLC. Peaks were identified by comparing the elution times with known standards of fatty acid methyl ester. Accordingly, cyanobacterial genes involved in fatty acid metabolism can be used to generate transgenic plants with altered fatty acid compositions.

EXAMPLE 7

Construction of Borage cDNA Library

Membrane bound polysomes were isolated from borage seeds 12 days post pollination (12 DPP) using the protocol established for peas by Larkins and Davies (1975 *Plant Phys.* 55:749-756). RNA was extracted from the polysomes as described by Mechler (1987 Methods in Enzymology 152:241-248, Academic Press).

Poly-A+ RNA was isolated from the membrane bound polysomal RNA by use of oligotex-dT beads (Qiagen). Corresponding cDNA was made using Stratagene's ZAP cDNA synthesis kit. The cDNA library was constructed in the lambda ZAP II vector (Stratagene) using the lambda ZAP II vector kit. The primary library was packaged in Gigapack II Gold packaging extract (Stratagene). The library was used to generate expressed sequence tags (ESTs), and sequences corresponding to the tags were used to scan the GenBank database.

EXAMPLE 8

Hybridization Protocol

Hybridization probes for screening the borage cDNA library were generated by using random primed DNA synthesis as described by Ausubel et al (1994 *Current Protocols in Molecular Biology*, Wiley Interscience, N.Y.) and corresponded to previously identified abundantly expressed seed storage protein cDNAs. Unincorporated nucleotides were removed by use of a G-50 spin column (Boehringer Manheim). Probe was denatured for hybridization by boiling in a water bath for 5 minutes, then quickly cooled on ice. Filters for hybridization were prehybridized at 60° C., for 2-4 hours in prehybridization solution (6XSSC [Maniatis et al 1984 Molecular Cloning A Laboratory Manual, Cold Spring Harbor Laboratory], 1X Denharts Solution, 0.05% sodium pyrophosphate, 100 µg/ml denatured salmon sperm DNA). Denatured probe was added to the hybridization solution (6X SSC, 1X Denharts solution, 0.05% sodium pyrophosphate, 100 µg/ml denatured salmon sperm DNA) and incubated at 60° C. with agitation overnight. Filters were washed in 4x, 2x, and 1x SET washes for 15 minutes each at 60° C. A 20X SET stock solution is 3M NaCl, 0.4M Tris base, 20 mM $Na_2EDTA-2H_2O$. The 4X SET wash was 4X SET, 12.5 mM $PO_4$, pH 6.8 and 0.2% SDS. The 2X SET wash was 2X SET, 12.5 mM $PO_4$, pH 6.8 and 0.2% SDS. The 1X SET wash was 1X SET, 12.5 mM $PO_4$, pH 6.8 and 0.2% SDS. Filters were allowed to air dry and were then exposed to X-ray film for 24 hours with intensifying screens at −80° C.

EXAMPLE 9

Random Sequencing of cDNAs from a Borage Seed (12 DPP) Membrane-bound Polysomal Library The borage cDNA library was plated at low density (500 pfu on 150 mm petri dishes). Highly prevalent seed storage protein cDNAs were "subtracted" by screening with the previously identified corresponding cDNAs. Non-hybridizing plaques were excised using Stratagene's excision protocol and reagents. Resulting bacterial colonies were used to inoculate liquid cultures and were either sequenced manually or by an ABI automated sequencer. Each cDNA was sequenced once and a sequence tag generated from 200-300 base pairs. All sequencing was performed by cycle sequencing (Epicentre). Over 300 ESTs were generated. Each sequence tag was compared to GenBank database by BLASTX computer program and a number of lipid metabolism genes, including the Δ6-desaturase were identified.

Database searches with a cDNA clone designated mbp-65 using BLASTX with the GenBank database resulted in a significant match to the Synechocystis Δ6desaturase. It was determined however, that this clone was not a full length cDNA. A full length cDNA was isolated using mbp-65 to screen the borage membrane-bound polysomal library. The sequence of the isolated cDNA was determined (FIG. 5A, SEQ ID NO:4) and the protein sequence of the open reading frame (FIG. 5B, SEQ ID NO:5) was compared to other known desaturases using Geneworks (IntelligGenetics) protein alignment program (FIG. 2). This alignment indicated that the cDNA was the borage Δ6-desaturase gene.

Figure 6:
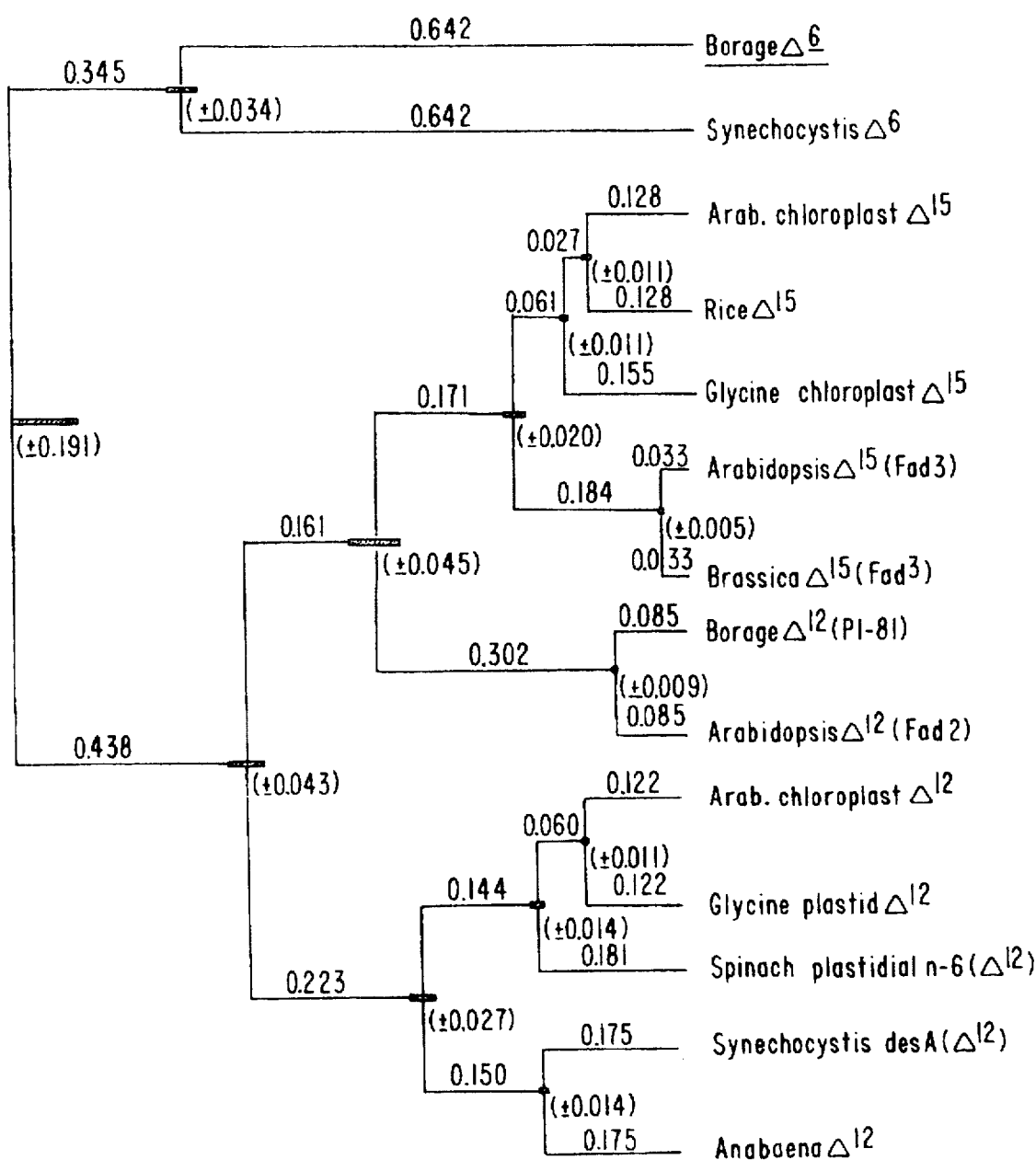
FIG. 6 is a dendrogram showing similarity of the borage Δ6-desaturase to other membrane-bound desaturases. The amino acid sequence of the borage Δ6-desaturase was compared to other known desaturases using Gene Works (IntelliGenetics). Numerical values correlate to relative phylogenetic distances between subgroups compared.

Although similar to other known plant desaturases, the borage delta 6-desaturase is distinct as indicated in the dendrogram shown in FIG. 6. Furthermore, comparison of the amino acid sequences characteristic of desaturases, particularly those proposed to be involved in metal binding (metal box 1 and metal box 2), illustrates the differences between the borage delta 6-desaturase and other plant desaturases (Table 3).

The borage delta 6-desaturase is distinguished from the cyanobacterial form not only in over all sequence (FIG. 6) but also in the lipid box, metal box 1 and metal box 2 amino acid motifs (Table 3). As Table 3 indicates, all three motifs are novel in sequence. Only the borage delta 6-desaturase metal box 2 shown some relationship to the Synechocystis delta-6 desaturase metal box 2.

In addition, the borage delta 6-desaturase is also distinct from another borage desaturase gene, the delta-12 desaturase. P1-81 is a full length cDNA that was identified by EST analysis and shows high similarity to the Arabidopsis delta-12 desaturase (Fad 2). A comparison of the lipid box, metal box 1 and metal box 2 amino acid motifs (Table 3) in borage delta 6 and delta-12 desaturases indicates that little homology exists in these regions. The placement of the two sequences in the dendrogram in FIG. 6 indicates how distantly related these two genes are.

digested in 30 mls plasmolyzing solution (25 g/l KCl, 3.5 g/l $CaCl_2$—$H_2O$, 10 mM MES, pH 5.6 and 0.2M mannitol) with 1% cellulose, 0.1% pectolyase, and 0.1% dreisalase overnight, in the dark, at room temperature. Released protoplasts were filtered through a 150 μm mesh and pelleted by centrifugation (100x g, 5 min.) then washed twice in plasmolyzing solution. Protoplasts were counted using a double chambered hemocytometer. DNA was transfected into the protoplasts by PEG treatment as described by Nunberg and Thomas (1993 *Methods in Plant Molecular Biology and*

TABLE 3

Comparison of common amino acid motifs in membrane-bound desaturases

| Desaturase | Amino Acid Motif | | |
|---|---|---|---|
| | Lipid Box | Metal Box 1 | Metal Box 2 |
| Borage $\Delta^6$ | WIGHDAGH (SEQ. ID. NO: 6) | HNAHH (SEQ. ID. NO: 12) | FQIEHH (SEQ. ID. NO: 20) |
| Synechocystis $\Delta^6$ | NVGHDANH (SEQ. ID. NO: 7) | HNYLHH (SEQ. ID. NO: 13) | HQVTHH (SEQ. ID. NO: 21) |
| Arab. chloroplast $\Delta^{15}$ | VLGHDCGH (SEQ. ID. NO: 8) | HRTHH (SEQ. ID. NO: 14) | HVIHH (SEQ. ID. NO: 22) |
| Rice $\Delta^{15}$ | VLGHDCGH (SEQ. ID. NO: 8) | HRTHH (SEQ. ID. NO: 14) | HVIHH (SEQ. ID. NO: 22) |
| Glycine chloroplast $\Delta^{15}$ | VLGHDCGH (SEQ. ID. NO: 8) | HRTHH (SEQ. ID. NO: 14) | HVIHH (SEQ. ID. NO: 22) |
| Arab. fad3 ($\Delta^{15}$) | VLGHDCGH (SEQ. ID. NO: 8) | HRTHH (SEQ. ID. NO: 14) | HVIHH (SEQ. ID. NO: 22) |
| Brassica fad3 ($\Delta^{15}$) | VLGHDCGH (SEQ. ID. NO: 8) | HRTHH (SEQ. ID. NO: 14) | HVIHH (SEQ. ID. NO: 22) |
| Borage $\Delta^{12}$ (P1-81)* | VIAHECGH (SEQ. ID. NO: 9) | HRRHH (SEQ. ID. NO: 15) | HVAHH (SEQ. ID. NO: 23) |
| Arab. fad2 ($\Delta^{12}$) | VIAHECGH (SEQ. ID. NO: 9) | HRRHH (SEQ. ID. NO: 15) | HVAHH (SEQ. ID. NO: 23) |
| Arab. chloroplast $\Delta^{12}$ | VIGHDCAH (SEQ. ID. NO: 10) | HDRHH (SEQ. ID. NO: 16) | HIPHH (SEQ. ID. NO: 24) |
| Glycine plastid $\Delta^{12}$ | VIGHDCAH (SEQ. ID. NO: 10) | HDRHH (SEQ. ID. NO: 16) | HIPHH (SEQ. ID. NO: 24) |
| Spinach plastidial n-6 | VIGHDCAH (SEQ. ID. NO: 10) | HDQHH (SEQ. ID. NO: 17) | HIPHH (SEQ. ID. NO: 24) |
| Synechocystis $\Delta^{12}$ | VVGHDCGH (SEQ. ID. NO: 11) | HDHHH (SEQ. ID. NO: 18) | HIPHH (SEQ. ID. NO: 24) |
| Anabaena $\Delta^{12}$ | VLGHDCGH (SEQ. ID. NO: 8) | HNHHH (SEQ. ID. NO: 19) | HVPHH (SEQ. ID. NO: 25) |

*P1-81 is a full length cDNA which was identified by EST analysis and shows high similarity to the Arbidopsis Δ12 desaturase (fad2)

EXAMPLE 10

Construction of 222.1Δ⁶NOS for Transient and Expression

Figure 7:
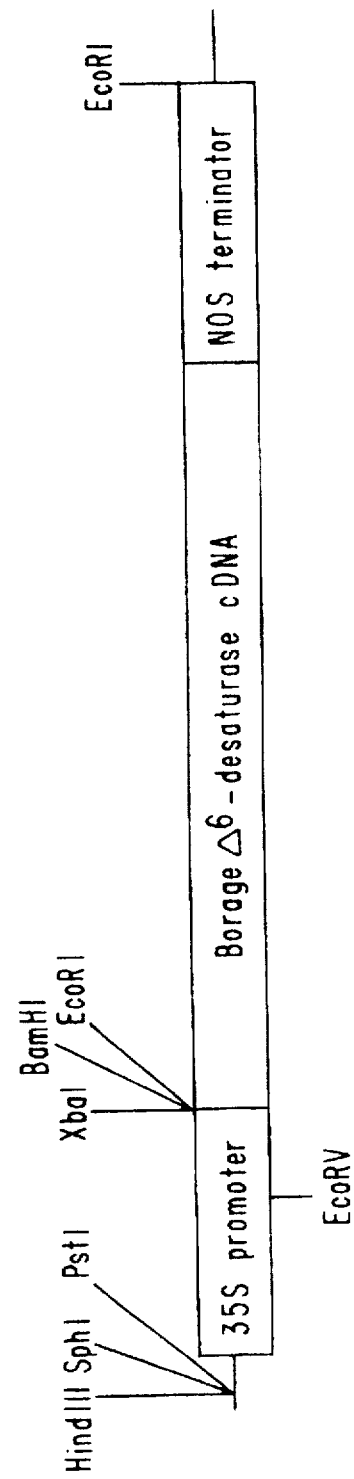
FIG. 7 is a restriction map of 221.Δ6.NOS and 121.Δ6.NOS. In 221.Δ6.NOS, the remaining portion of the plasmid is pBI221 and in 121.Δ6.NOS, the remaining portion of the plasmid is pBI121.

The vector pBI221 (Jefferson et al. 1987 EMBO J. 6:3901-3907) was prepared for ligation by digestion with BamHI and EcoICR I (Promega) which excises the GUS coding region leaving the 35S promoter and NOS terminator intact. The borage Δ 6-desaturase cDNA was excised from the Bluescript plasmid (Stratagene) by digestion with BamHI and XhoI. The XhoI end was made blunt by use of the Klenow fragment. This fragment was then cloned into the BamHI/EcoICR I sites of pBI221, yielding 221.Δ⁶NOS (FIG. 7). In 221.Δ⁶.NOS, the remaining portion (backbone) of the restriction map depicted in FIG. 7 is pBI221.

EXAMPLE 11

Construction of 121.Δ⁶.NOS for Stable Transformation

The vector pBI121 (Jefferson et al. 1987 EMBO J. 6:3901-3907) was prepared for ligation by digestion with BamHI and ECOICR I (Promega) which excises the GUS coding region leaving the 35S promoter and NOS terminator intact. The borage Δ 6-desaturase cDNA was excised from the Bluescript plasmid (Stratagene) by digestion with BamHI and XhoI. The XhoI end was made blunt by use of the Klenow fragment. This fragment was then cloned into the BamHI/EcoICR I sites of pBI121, yielding 121.1Δ⁶NOS (FIG. 7). In 121.Δ⁶.NOS, the remaining portion (backbone) of the restriction map depicted in FIG. 7 is pBI121.

EXAMPLE 12

Transient Expression

All work involving protoplasts was performed in a sterile hood. One ml of packed carrot suspension cells were

*Biotechnology*, B. R. Glick and J. E. Thompson, eds. pp. 241-248) using $10^6$ protoplasts and 50-70 ug of plasmid DNA (221.Δ6.NOS). Protoplasts were cultured in 5 mls of MS media supplemented with 0.2M mannitol and 3 μm 2,4-D for 48 hours in the dark with shaking.

EXAMPLE 13

Stable Transformation of Tobacco

121.Δ⁶.NOS plasmid construction was used to transform tobacco (Nicotiana tabacum cv. xanthi) via Agrobacterium according to standard procedures (Horsh et al., 1985 Science 227: 1229-1231; Bogue et al., 1990 Mol. Gen. Genet. 221:49-57), except that initial transformants were selected on 100 ug/ml kanamycin.

EXAMPLE 14

Preparation and Analysis of Fatty Acid Methyl Esters (FAMEs)

Tissue from transfected protoplasts and transformed tobacco plants was frozen in liquid nitrogen and lyophilized overnight. FAMEs were prepared as described by Dahmer et al (1989 J. Amer. Oil Chem. Soc. 66:543-548). In some cases, the solvent was evaporated again, and the FAMEs were resuspended in ethyl acetate and extracted once with deionized water to remove any water soluble contaminants. The FAMEs were analyzed by gas chromatography (GC) on a J&W Scientific DB-wax column (30 m length, 0.25 mm ID, 0.25 um film).

Figure 9A:
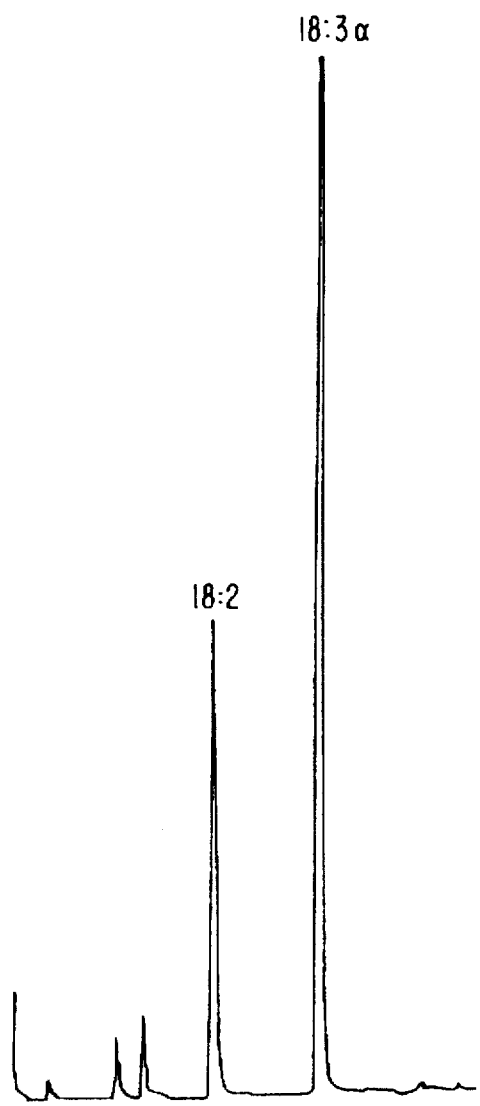
FIG. 9 provides gas liquid chromatography profiles of an untransformed tobacco leaf (Panel A) and a tobacco leaf transformed with 121.Δ6.NOS (Panel B). The positions of 18:2, 18:3 α, 18:3γ (GLA), and 18:4 are indicated.
Figure 9B:
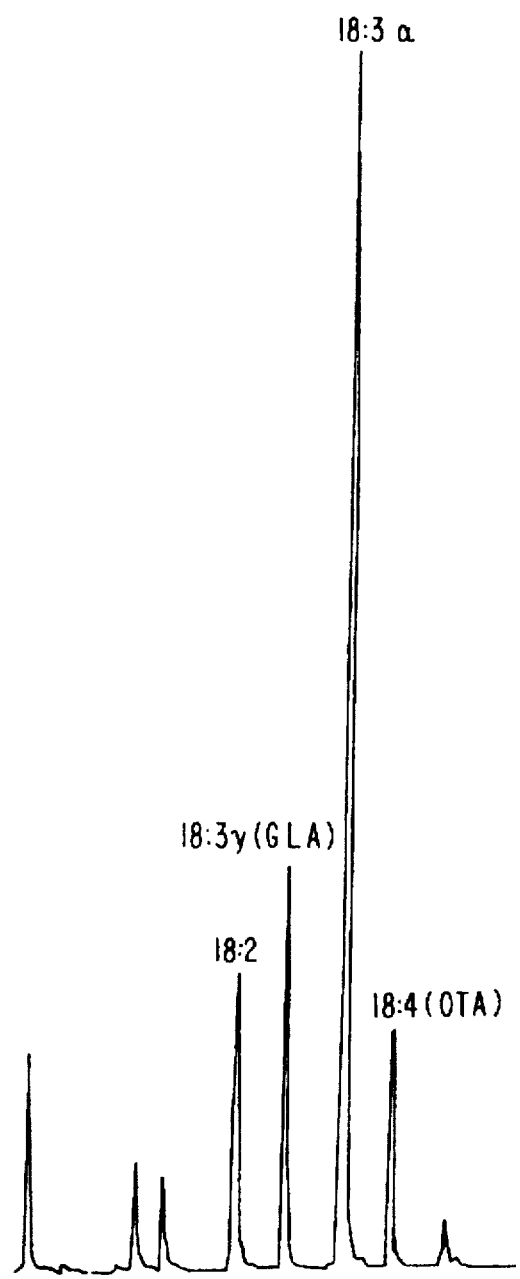

An example of a transient assay is shown in FIG. 8 which represents three independent transfections pooled together. The addition of the borage Δ6-desaturase cDNA corresponds with the appearance of gamma linolenic acid (GLA) which is one of the possible products of Δ6-desaturase. Furthermore, transgenic tobacco containing the borage Δ6-desaturase driven by the cauliflower mosaic virus 35S promoter also produce GLA as well as octa-decaenoic acid (18:4) which is formed by the further desaturation of GLA (FIG. 9). These results indicate that the borage delta 6-desaturase gene can be used to transform plant cells to achieve altered fatty acid compositions.

What is claimed:

1. An isolated borage Δ6-desaturase which comprises the amino acid sequence of SEQ ID No: 5.

* * * * *

UNITED STATES PATENT AND TRADEMARK OFFICE
CERTIFICATE OF CORRECTION

PATENT NO. : 5,789220
DATED : August 4, 1998
INVENTOR(S) : Terry Thomas, et al.

It is certified that error appears in the above-identified patent and that said Letters Patent are hereby corrected as shown below:

Column 5, Line 33: "12,15)" should be in superscript.

Signed and Sealed this

Twenty-ninth Day of May, 2001

*Attest:*

NICHOLAS P. GODICI

*Attesting Officer*    *Acting Director of the United States Patent and Trademark Office*